(12) United States Patent
Degani

(10) Patent No.: US 10,026,173 B2
(45) Date of Patent: *Jul. 17, 2018

(54) DIFFUSION ELLIPSOID MAPPING OF TISSUE

(71) Applicant: DDE MRI Solutions Ltd., Tel Aviv (IL)

(72) Inventor: Hadassa Degani, Tel Aviv (IL)

(73) Assignee: DDE MRI SOLUTIONS LTD., Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/723,251

(22) Filed: Oct. 3, 2017

(65) Prior Publication Data

US 2018/0130204 A1 May 10, 2018

Related U.S. Application Data

(63) Continuation-in-part of application No. 15/344,518, filed on Nov. 6, 2016, now Pat. No. 9,922,421.

(51) Int. Cl.
*G06T 7/00* (2017.01)
*G06T 19/20* (2011.01)
(Continued)

(52) U.S. Cl.
CPC ............ *G06T 7/0012* (2013.01); *A61B 5/004* (2013.01); *A61B 5/055* (2013.01); *G06T 15/08* (2013.01);
(Continued)

(58) Field of Classification Search
CPC .......... G01R 33/56341; G01R 33/4806; A61B 5/055; A61B 2576/056; A61B 5/0042;
(Continued)

(56) References Cited

U.S. PATENT DOCUMENTS 6,724,190 B2 4/2004 van Muiswinkel et al.
8,452,373 B2 5/2013 Wyrwicz et al.
(Continued)

FOREIGN PATENT DOCUMENTS

WO 2007112319 10/2007
WO 2009129200 10/2009

OTHER PUBLICATIONS

Basser et al., (1994) MR diffusion tensor spectroscopy and imaging. Biophysical Journal, 1(66), 259-267.
(Continued)

*Primary Examiner* — Haixia Du
(74) *Attorney, Agent, or Firm* — The Roy Gross Law Firm, LLC; Roy Gross

(57) ABSTRACT

Methods and devices for generating novel diffusion ellipsoid maps from diffusion tensor imaging (DTI) scan data. One example method includes: (i) generating, from DTI scan data, for each voxel in a plurality of voxels in one or more slabs of a target tissue, a respective diffusion tensor; (ii) generating, for each voxel, eigenvalues and eigenvectors of the respective diffusion tensor and a respective set of diffusion parameters; (iii) partitioning the voxels into two groups, wherein voxels, whose respective set of diffusion parameters is such that each element in the set is smaller than a corresponding element in a set of thresholds, are substantially all in a first group of the two groups; and (iv) providing a graphical representation of a diffusion ellipsoid map of at least one of the one or more slabs, wherein ellipsoids, associated with voxels in the first group, are displayed differently to the other ellipsoids. The utility of the disclosed methods and devices in breast cancer and prostate cancer detection is demonstrated.

15 Claims, 25 Drawing Sheets
(21 of 25 Drawing Sheet(s) Filed in Color)

(51) Int. Cl.
  *G06T 15/08* (2011.01)
  *A61B 5/00* (2006.01)
  *A61B 5/055* (2006.01)
(52) U.S. Cl.
  CPC .... *G06T 19/20* (2013.01); *G06T 2207/10092* (2013.01); *G06T 2207/30024* (2013.01); *G06T 2207/30068* (2013.01); *G06T 2207/30081* (2013.01); *G06T 2219/2012* (2013.01)
(58) Field of Classification Search
  CPC .......... A61B 5/742; G06T 2207/10092; G06T 2207/10088; G06T 2210/41
  See application file for complete search history.

(56) References Cited

U.S. PATENT DOCUMENTS

| | | |
|---|---|---|
| 8,526,698 B2 | 9/2013 | Degani et al. |
| 2006/0189865 A1 | 8/2006 | Guhring et al. |
| 2013/0085383 A1* | 4/2013 | Fei .......................... A61B 8/12 600/424 |

OTHER PUBLICATIONS

Cabarrus & Westphalen, (2017) Multiparametric magnetic resonance imaging the of prostate—a basic tutorial. Translational Andrology and Urology 6(3):376-386.
Degani Hadassa, Diffusion MRI of the Breast. Erasmus Course on Magnetic Resonance Image, EMRI, Breast and Female Imaging Erasmus Course Valencia. Valencia May 14-16, 2015. 61 Pages.
Eyal et al., (2008) 3-D Tracking of the Mammary Ductal Tree Using Diffusion Tensor MR Imaging. Proc Intl Soc Mag Reson Med 16: 588.
Eyal et al., (2012) Parametric diffusion tensor imaging of the breast. Investigative radiology, 47(5), 284-291.
Furman-Haran et al., (2012) Advantages and drawbacks of breast DTI. European journal of radiology, 81, S45-S47.
Furman-Haran et al., (2016) Can diffusion tensor anisotropy indices assist in breast cancer detection? J Magn Reson Imaging44(6): 1624-1632.
Ghosh et al., (2009) Ternary Quartic approach for positive 4th order diffusion tensors revisited. IEEE, ISBI, pp. 618-621.
Gürses et al., (2011) Diagnostic utility of DTI in prostate cancer. European journal of radiology, 79(2), 172-176.
Degani Hadassa, Developing prostate DTI for early detection and diagnosis of cancer in the prostate. Retrieved from the internet on Dec. 6, 2017, URL: https://www.weizmann.ac.il/Biological_Regulation/degani/research-activities/developing-prostate-dti-early-detection-and-diagnosis-cancer-prostate; 1 page.
Holdsworth et al., (2008) Readout-segmented EPI for rapid high resolution diffusion imaging at 3T. European journal of radiology, 65(1), 36-46.
Jiang et al., (2006) DtiStudio: resource program for diffusion tensor computation and fiber bundle tracking. Comput Methods Programs Biomed 81(2): 106-116.
Kim et al., (2012) Diffusion tensor imaging of normal prostate at 3 T: effect of number of diffusion-encoding directions on quantitation and image quality. The British journal of radiology, 85(1015), e279-e283.
Kingsley (2006) Introduction to Diffusion Tensor Imaging Mathematics: Part II. Anisotropy, Diffusion Weighting Factors, and Gradient Encoding Schemes. Concepts in Magnetic Resonance Part A 28A(2): 123-154.
Kingsley (2006) Introduction to diffusion tensor imaging mathematics: Part III. Tensor calculation, noise, simulations, and optimization. Concepts in Magnetic Resonance Part A 28A(2): 155-179.
Kozlowski et al., (2010) Combined prostate diffusion tensor imaging and dynamic contrast enhanced MRI at 3T—quantitative correlation with biopsy. Magnetic resonance imaging, 28(5), 621-628.
Kroenke et al., (2006) Modeling water diffusion anisotropy within fixed newborn primate brain using Bayesian probability theory. Magn Reson Med 55(1): 187-197.
Landman et al., (2007) Effects of diffusion weighting schemes on the reproducibility of DTI-derived fractional anisotropy, mean diffusivity, and principal eigenvector measurements at 1.5T. Neuroimage 36(4): 1123-38.
Le Bihan et al., (2001) Diffusion Tensor Imaging: Concepts and Applications. Journal of Magnetic Resonance Imaging 13: 534-546.
Li et al., (2011) Diffusion tensor imaging of prostate at 3.0 Tesla. Acta Radiologica, 52(7), 813-817.
Li et al., (2014) Detection of prostate cancer in peripheral zone: comparison of MR diffusion tensor imaging, quantitative dynamic contrast-enhanced MRI, and the two techniques combined at 3.0 T. Acta Radiologica, 55(2), 239-247.
Li et al., (2015) Correlation of gleason scores with magnetic resonance diffusion tensor imaging in peripheral zone prostate cancer. Journal of Magnetic Resonance Imaging, 42(2), 460-467.
Manenti et al., (2007) Diffusion tensor magnetic resonance imaging of prostate cancer. Investigative radiology, 42(6), 412-419.
Marini et al., (2007) Quantitative diffusion weighted MR imaging in the differential diagnosis of breast lesion. Eur Radial 17:2646-2655.
Metz et al., (1998) Maximum likelihood estimation of receiver operating characteristic (ROC) curves from continuously-distributed data. Statistics in medicine, 17(9), 1033-1053.
Mukherjee et al., (2008) Diffusion tensor MR imaging and fiber tractography: theoretic underpinnings. AJNR Am J Neuroradiol 29(4): 632-41.
Nissan et al., (2014) Diffusion-tensor MR imaging of the breast: hormonal regulation. Radiology, 271(3), 672-680.
Nissan et al., (2014) Tracking the Mammary Architectural Features and Detecting Breast Cancer with Magnetic Resonance Diffusion Tensor Imaging. JoVE (Journal of Visualized Experiments), (94), e52048.
Pajevic and Pierpaoli (1999) Color schemes to represent the orientation of anisotropic tissues from diffusion tensor data: Application to white matter fiber tract mapping in the human brain. Magnetic Resonance in Medicine 42(3): 526-540.
Park et al., (2014) Diffusion-tensor MRI at 3 T: differentiation of central gland prostate cancer from benign prostatic hyperplasia. American Journal of Roentgenology, 202(3), W254-W262.
Partridge et al., (2006) Diffusion Tensor Imaging of the Breast: Preliminary Clinical Findings. Proc Intl Soc Mag Reson Med 14: 2902.
Reese et al., (2003) Reduction of eddy-current-induced distortion in diffusion MRI using a twice-refo170cused spin echo. Magnetic Resonance in Medicine, 49(1), 177-182.
Rubesova et al., (2006) Quantitative diffusion imaging in breast cancer: a clinical prospective study. J Magn Reson Imaging 24(2): 319-24.
Shapiro-Feinberg et al., (2012) Clinical results of DTI. European journal of radiology, 81, S151-S152.
Sinha & Sinha, (2004) In vivo diffusion tensor imaging of the human prostate. Magnetic resonance in medicine, 52(3), 530-537.
Solomon et al., (2015) Overcoming limitations in diffusion-weighted MRI of breast by spatio-temporal encoding. Magnetic resonance in medicine, 73(6), 2163-2173.
Stejska & Tanner, (1965) Spin diffusion measurements: spin echoes in the presence of a time-dependent field gradient. The journal of chemical physics, 42(1), 288-292.
Teruel et al., (2016) Diffusion weighted imaging for the differentiation of breast tumors: From apparent diffusion coefficient to high order diffusion tensor imaging. Journal of magnetic resonance imaging: JMRI, 43(5), 1111-1121.
Turner et al., (1990) Echo-planar imaging of intravoxel incoherent motion. Radiology, 177(2), 407-414.
Turner et al., (1991) Echo-planar imaging of diffusion and perfusion. Magnetic resonance in medicine, 19(2), 247-253.
Wenkel et al., (2007) Diffusion-Weighted Imaging in Breast MRI—An Easy Way to Improve Specificity. Magnetom Flash Mar. 2007 pp. 28-32.

(56) References Cited

OTHER PUBLICATIONS

Xu et al., (2009) Magnetic resonance diffusion characteristics of histologically defined prostate cancer in humans. Magnetic resonance in medicine, 61(4), 842-850.

* cited by examiner

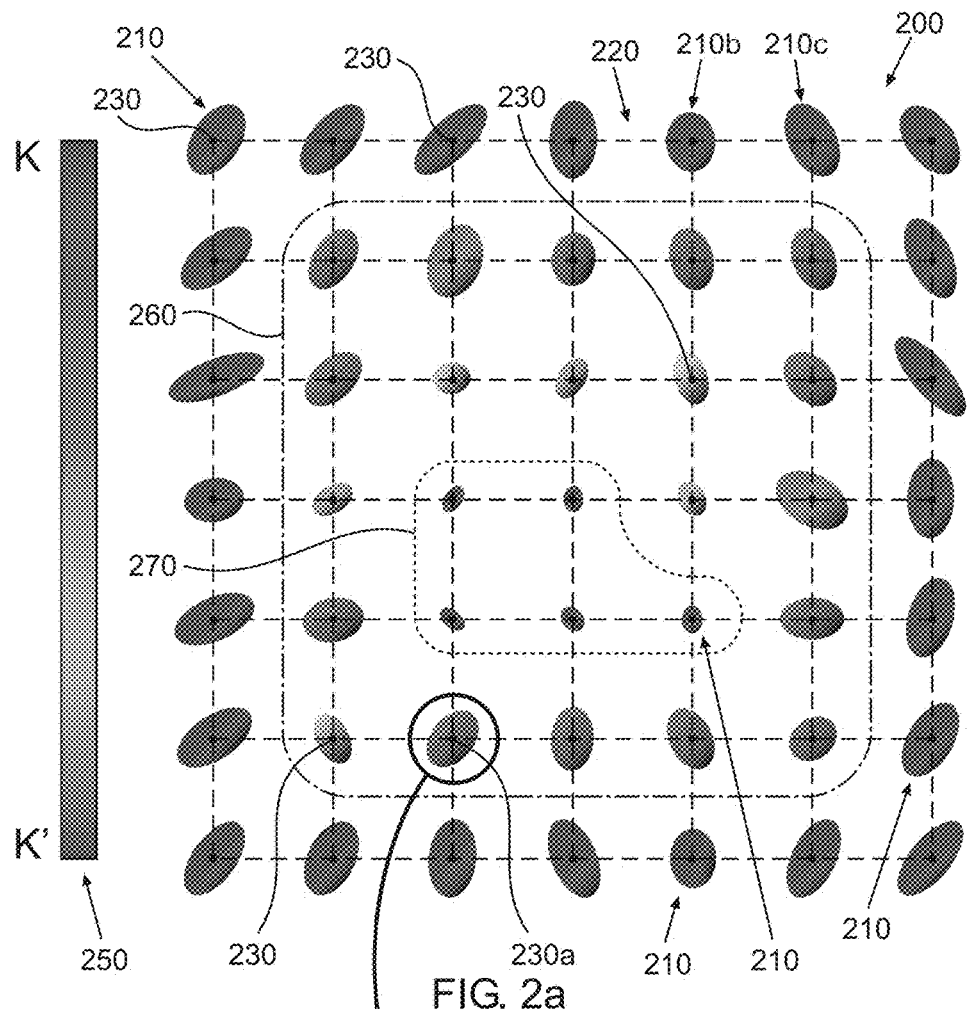
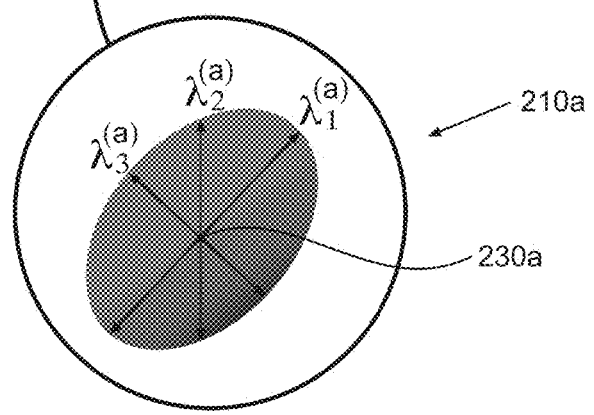
FIG. 2a
FIG. 2b

DIFFUSION ELLIPSOID MAPPING OF TISSUE

FIELD OF THE INVENTION

The present disclosure, according to some embodiments, relates to the field of diffusion tensor magnetic resonance imaging of a target tissue of a subject, and more particularly, but not exclusively, to diffusion ellipsoid mappings of the target tissue of the subject.

BACKGROUND OF THE INVENTION

Diffusion-weighted imaging (DWI) is a magnetic resonance imaging (MRI) technique for mapping the diffusion of molecules, such as water, within biological tissue. Diffusion tensor imaging (DTI) is subfield of DWI, which has been used extensively to map white matter tractography in the brain.

DTI scan data is sometimes presented as a diffusion ellipsoid map. Each ellipsoid is associated with a respective voxel in a slice of the imaged tissue, and is accordingly centered about map coordinates corresponding to the centerpoint of the respective voxel in the slice (such that all the ellipsoids, which are three-dimensional, are centered about respective map coordinates on a single flat plane—the map plane). The dimensions and orientation of each ellipsoid are determined by the diffusion tensor associated with the respective voxel (see, for example, Basser et al., Biophysical Journal, 66, p. 259, 1994). More specifically, the length and orientation of each of the three principal axes of an ellipsoid are determined by a respective eigenvalue-eigenvector pair of the associated diffusion tensor. The eigenvalues $\lambda_1$, $\lambda_2$, and $\lambda_3$ (usually defined such that $\lambda_1 \geq \lambda_2 \geq \lambda_3$) equal the diffusion coefficients along three orthogonal directions defined by the corresponding eigenvectors $v_1$, $v_2$, and $v_3$, respectively.

Typically, in DTI brain imaging, each ellipsoid is colored according to the direction (i.e. $v_1$) in which the respective largest principal axis (having a length $\lambda_1$ or a length proportional to $\lambda_1$, including, but not limited to, $\sqrt{\lambda_1}$) thereof points, as well as including light and shade effects to better visually impart the three-dimensional shape thereof. For example, if the largest principal axis is closest to the x-axis, y-axis, or z-axis (of a laboratory, Cartesian frame of reference), the ellipsoid is colored in either blue, red, or green, respectively. In some ellipsoid maps, the ellipsoids may be colored as a combination of blue, red, and green, weighted according to the proximity of the largest principal axis to each of the respective axes of the laboratory frame.

The past decade has seen the application of DWI, including DTI, to cancer detection, e.g. in the breast and the prostate. Water diffusion in mammary ducts and lobules in the breast is anisotropic, being fast along the length of a duct/lobule and restricted in directions perpendicular to the length of the duct/lobule. Without being bound to any theory or mechanism, the presence of cancer cells in a region of the breast is believed to bring about the blockage/partial blockage and physical deformation of mammary ducts/lobules and the surroundings thereof in the region, with a resultant reduction in the diffusion rate, and the anisotropy of the diffusion, through the mammary ducts/lobules. Accordingly, low $\lambda_1$ values have been found to be indicative of breast cancer. Alternatively, or in addition, the absolute maximal anisotropy index, defined as $\lambda_1$-$\lambda_3$, assumes low values in the presence of breast cancer. See E. Eyal et al., Invest. Radiol. 2012 47(5):284-91; N. Nissan et al., J. Vis. Exp. (94), e52048, 2014; E. Furman-Haran et al., J. Magn. Reson. Imaging, 44: 1624-1632, 2016; E. Furman-Haran et al., Europ. J Radiol. 81, S 45-47, 2012; and M. Shapiro Feinberg et al., Europ. J Radiol. S 151-152, 2012. The contents of all the above-cited publications is incorporated herein by reference.

Diffusion ellipsoid maps of the breast were presented in J. R. Teurel et al., J. Magn. Reson. Imaging, 2016 May; 43(5):1111-21, the contents of which are incorporated herein by reference, and in Furman-Haran et al., 2016, ibid. In the former publication, the diffusion ellipsoids were all colored in the same color. In the latter publication, the diffusion ellipsoids were colored according to the orientation of the respective largest principal axis, as elaborated on above for brain imaging.

The utility of DTI in differentiating central gland prostate cancer from benign prostatic hyperplasia was demonstrated, for example, in S. Y. Park et al., AJR 2014; 202:W254-W262, with low values of the apparent diffusion coefficient (ADC) and high values of the fractional anisotropy (FA) being indicative of malignant tumors. The utility of DTI in estimating tumor aggressiveness in peripheral zone prostate cancer was demonstrated in Liang Li et al. (J. Magn. Reson. Imaging, 42:460-467, 2015) with FA values and ADC values from cancerous (peripheral) zones being positively and negatively correlated, respectively, with the Gleason score.

Low values of $\lambda_1$, $\lambda_2$, and $\lambda_3$ have also been found to be indicative of prostate cancer.

The contents of the above publications are included herein by reference.

U.S. Pat. No. 8,526,698 to Degani, the contents of which are incorporated herein by reference, discloses a method, apparatus and computer product for imaging a human breast to map the breast ductal tree. First, a breast is diffusion tensor imaged with high spatial resolution. Then the breast ductal tree is tracked using a protocol for: breast based on echo-planar imaging (EPI) diffusion designed for optimizing diffusion weightings (b values), number of non-collinear directions for tensor calculations, diffusion, echo and repetition times, spatial resolution, signal to noise, scanning time, and a sequence for fat suppression. The diffusion tensor is calculated by a non-linear best fit algorithm and then diagonalized (e.g. using principal component analysis) to obtain three eigenvectors and their corresponding eigenvalues. A vector field map is obtained for tracking of breast ducts of the ductal trees along the direction of the 1st eigenvector $v_1$ and the ductal tree is displayed on a voxel by voxel basis in parametric images using color coding and vector pointing.

SUMMARY OF THE INVENTION

Aspects of the present disclosure, according to some embodiments thereof, relate to diffusion ellipsoid mappings of a target tissue of a subject. More specifically, aspects of the present disclosure, according to some embodiments thereof, relate to diffusion ellipsoid mappings of (i) a breast, or a portion thereof, of a female subject, or (ii) a prostate, or a portion thereof, of a male subject.

As discussed above, in brain imaging, DTI scan data is sometimes presented in terms of diffusion ellipsoid maps. These maps convey information regarding the diffusion in a respective slab of a target tissue through the three-dimensional graphical-rendering of the ellipsoids, as well as through the coloring of the ellipsoids, as explained above. Such rendering and coloring, however, may, in some cases, not convey full information regarding the magnitude of the diffusion in each of the voxels. For example, if the largest principal axis of a diffusion ellipsoid is substantially perpendicular to the map plane, then the map will convey substantially no information with respect to the magnitude of the diffusion perpendicularly to the map plane (other than the diffusion rate in that direction being greater than along the other axes), and, hence, incomplete information regarding the anisotropy of the diffusion. In particular, a pair of ellipsoids may appear indistinguishable even if the largest principal axis of one substantially differs in length from that of other. Such lack of information can potentially complicate cancer evaluation based on the above-mentioned diffusion ellipsoid maps. To compensate for this lack of information, the radiologist may have to look at another image of the slice (depicted in the diffusion ellipsoid map), for example, a two-dimensional image of the slice wherein each voxel (or more precisely pixel since the image is two-dimensional) is colored according to e.g. the value of the apparent diffusion coefficient associated therewith. Accordingly, the total number of images that the radiologist has to review may be doubled, for example, from 60 to 120 when the target tissue is partitioned into 60 slabs.

Advantageously, according to some embodiments, the ellipsoid maps disclosed herein are characterized in that the ellipsoids are colored according to a magnitude, rather than an orientation, of the diffusion in the respective voxel, thereby potentially avoiding having to review more than a single image of a slice. For example, according to some embodiments, some of the diffusion ellipsoids, having a value of $\lambda_1$ greater than a threshold value, are colored in a first color, while the remaining ellipsoids are colored in a color scale, according to the value of $\lambda_1$. The first color may be located to at the top end of color scale, such as to correspond to the value of the threshold, or may constitute a color not included in the color scale. In particular, values of $\lambda_1$ smaller than the threshold may be indicative of cancer.

According to some embodiments, the diffusion ellipsoid maps and methods disclosed herein may be used for detection of breast cancer.

According to some embodiments, the diffusion ellipsoid maps and methods disclosed herein may be used for characterization of breast cancer.

According to some embodiments, the diffusion ellipsoid maps and methods disclosed herein may be used for evaluation of breast cancer staging.

According to some embodiments, the diffusion ellipsoid maps and methods disclosed herein may be used for distinguishing benign breast tumors from malignant breast tumors.

According to some embodiments, the diffusion ellipsoid maps and methods disclosed herein may be used for detection of prostate cancer.

According to some embodiments, the diffusion ellipsoid maps and methods disclosed herein may be used for characterization of prostate cancer.

According to some embodiments, the diffusion ellipsoid maps and methods disclosed herein may be used for evaluation of prostate cancer staging.

According to some embodiments, the diffusion ellipsoid maps and methods disclosed herein may be used for distinguishing benign prostate tissue from malignant prostate tumors.

According to some embodiments, the diffusion ellipsoid maps and methods disclosed herein may be used for mapping internal body organs, and diffusion processes therein, even in non-cancer related applications, such as in the mapping of neural tracts in the brain.

Thus, according to an aspect of some embodiments, there is provided a computer-implemented method of mapping a target tissue of a subject. The method includes:

Providing diffusion tensor imaging (DTI) scan data of a plurality of voxels in one or more slabs of a target tissue of a subject.

Calculating a respective diffusion tensor for each voxel in the plurality of voxels in the target tissue.

Determining, for each voxel, eigenvalues and eigenvectors of the respective diffusion tensor and a respective set of diffusion parameters, wherein the respective set of diffusion parameters associated with each voxel is indicative of a magnitude and/or anisotropy or isotropy of the diffusion in the voxel.

Partitioning the voxels into two groups, a first group and a second group, wherein the voxels, whose respective set of diffusion parameters is such that each diffusion parameter is less than a corresponding element in a set of thresholds, are substantially all in the first group.

Generating a graphical representation of a diffusion ellipsoid map made from diffusion ellipsoids associated with the first group and the second group of voxels of at least one of the one or more slabs of the target tissue, wherein the diffusion ellipsoids associated with voxels in the first group are colored differently to the diffusion ellipsoids associated with the second group.

According to some embodiments of the method, voxels whose respective set of diffusion parameters is such that at least one of the diffusion parameters is greater than, or equal to, a corresponding element in the set of thresholds are substantially all in the second group.

According to some embodiments of the method, the respective set of diffusion parameters, associated with each voxel, includes a diffusion rate parameter substantially equal to a convex combination of the eigenvalues of the voxel or to an apparent diffusion coefficient.

According to some embodiments of the method, each diffusion ellipsoid corresponding to the first group is displayed in a color scale, corresponding to the magnitude of the diffusion rate parameter.

According to some embodiments of the method, each diffusion ellipsoid corresponding to the second group is displayed in a color from the group consisting of a color not in the color scale and a color at the upper end of the color scale.

According to some embodiments of the method, diffusion ellipsoids corresponding to the first group, whose respective diffusion parameter is smaller than a lower threshold, are displayed in a color at the bottom end of the color scale. The color scale is scaled such that the bottom end thereof corresponds to the lower threshold, and the top end thereof corresponds to the element in the set of thresholds associated with the diffusion rate parameter.

According to some embodiments of the method, the diffusion rate parameter is selected from the group consisting of substantially $\lambda_1$ and substantially $<\lambda>$.

According to some embodiments of the method, diffusion ellipsoid maps including adjacent diffusion ellipsoids belonging to the first group, are indicative of cancer in the target tissue.

According to some embodiments of the method, the subject is female and the target tissue is a breast or a portion thereof.

According to some embodiments of the method, the subject is male and the target tissue is a prostate or a portion thereof.

According to some embodiments of the method, diffusion ellipsoid maps including adjacent diffusion ellipsoids belonging to the first group are indicative of a malignant tumor in the target tissue.

According to some embodiments of the method, wherein the target tissue is breast tissue, diffusion ellipsoid maps including adjacent diffusion ellipsoids belonging to the first group are indicative of a malignant tumor in the breast tissue.

According to some embodiments of the method, wherein the target tissue is prostate tissue, diffusion ellipsoid maps including adjacent diffusion ellipsoids belonging to the first group are indicative of a malignant tumor in the prostate tissue.

According to some embodiments of the method, diffusion ellipsoid maps including adjacent ellipsoids, which are displayed in a color corresponding to the bottom end of a color scale, are indicative of a more aggressive malignant tumor in the target tissue, as compared to diffusion ellipsoid maps including adjacent ellipsoids belonging to the first group, but which do not include adjacent ellipsoids displayed in the color corresponding to the bottom end of the color scale, wherein the respective set of diffusion parameters, associated with each voxel, includes a diffusion rate parameter substantially equal to a convex combination of the eigenvalues of the voxel or to the apparent diffusion coefficient associated therewith, and wherein the color scale corresponds to the magnitude of the diffusion rate parameter.

According to some embodiments of the method, wherein the target tissue is breast tissue, the set of diffusion parameters includes an anisotropy parameter indicative of an anisotropy of the diffusion within a voxel.

According to some embodiments of the method, wherein the target tissue is breast tissue, the anisotropy parameter is substantially $\lambda_1$-$\lambda_3$.

According to some embodiments of the method, wherein the target tissue is prostate tissue, the set of diffusion parameters includes an isotropy parameter indicative of an isotropy of the diffusion within a voxel.

According to some embodiments of the method, wherein the target tissue is breast tissue, the anisotropy parameter is selected from the group consisting of substantially FA, substantially RA, and substantially 1-VR.

According to some embodiments of the method, wherein the target tissue is prostate tissue, the isotropy parameter is selected from the group consisting of substantially 1-FA, substantially 1-RA, and substantially VR.

According to some embodiments of the method, in the step of generating the graphical representation, diffusion ellipsoids corresponding to the second group are not displayed.

According to some embodiments of the method, the thresholds are predetermined thresholds.

According to some embodiments of the method, the diffusion tensor is a $4^{th}$-order tensor according to the $4^{th}$-order DTI model.

According to some embodiments of the method, the method further includes acquiring DTI scan data of the plurality of voxels in the one or more slabs of the target tissue, prior to the determining from the DTI scan data, for each voxel, the respective diffusion tensor.

According to some embodiments of the method, substantially only voxels, associated with DTI scan data above a maximum noise level, are included in the plurality of voxels.

According to some embodiments of the method, the second group of voxels is partitioned into at least two subgroups, according to respective values of the set of diffusion parameters of the voxels in the second group.

According to some embodiments of the method, the set of diffusion parameters consists of a diffusion rate parameter and an anisotropy/isotropy parameter and the second group is partitioned into two subgroups, a first subgroup and a second subgroup, and wherein voxels, whose diffusion rate parameter is smaller than the respective corresponding element in the set of thresholds, are substantially all in the first subgroup, and wherein voxels, whose diffusion rate parameter is greater than the respective corresponding element in the set of thresholds, are substantially all in the second subgroup.

According to some embodiments of the method, the method further includes superimposing the diffusion ellipsoids on at least one MRI image of the target tissue.

According to some embodiments of the method, the at least one MRI image of the target tissue is selected from the group consisting of a $T_2$-weighted image and a $T_1$-weighted image.

According to some embodiments of the method, the method further includes displaying the diffusion ellipsoid map on a graphical user interface (GUI).

According to some embodiments, the lengths of the axes of each diffusion ellipsoid are proportional to the eigenvalues, respectively, of the diffusion tensor associated with the diffusion ellipsoid.

According to some embodiments, the lengths of the axes of each diffusion ellipsoid are proportional to the square roots of the eigenvalues, respectively, of the diffusion tensor associated with the diffusion ellipsoid.

According to an aspect of some embodiments, a non-transitory computer readable medium is provided. The non-transitory computer readable medium has stored therein instructions executable by a computer system configured to implement one or more of the embodiments of the method specified above.

According to an aspect of some embodiments, a computer system is provided. The computer system includes the non-transitory computer readable medium specified above.

According to some embodiments of the computer system, the computer system further includes a display for displaying the diffusion ellipsoid maps in the step of generating the graphical representation.

According to an aspect of some embodiments, there is provided an image processing system for mapping a target tissue of a subject. The system includes a memory including computer executable instructions and data, and a processor functionally coupled to the memory and configured by the computer executable instructions. The processor is able to:

Receive DTI scan data of a plurality of voxels in one or more slabs of a target tissue of a subject.

Calculate, from the DTI scan data, a respective diffusion tensor for each voxel in the plurality of voxels in one or more slabs of the target tissue.

Determine, for each voxel, eigenvalues and eigenvectors of the respective diffusion tensor and a respective set of diffusion parameters, wherein the respective set of diffusion parameters associated with each voxel is indicative of a magnitude and/or anisotropy or isotropy of the diffusion in the voxel.

Partition the voxels into two groups, a first group and a second group, wherein the voxels, whose respective set of diffusion parameters is such that each diffusion parameter is less than a corresponding element in a set of thresholds, are substantially all in the first group.

Generate a graphical representation of a diffusion ellipsoid map of at least one of the one or more slabs made from diffusion ellipsoids associated with the first group and the second group of voxels, wherein the diffusion ellipsoids, associated with voxels in the first group, are colored differently to the diffusion ellipsoids associated with voxels in the second group.

According to some embodiments of the image processing system, the target tissue is breast tissue.

According to some embodiments of the image processing system, the target tissue is prostate tissue.

According to some embodiments of the image processing system, the respective set of diffusion parameters, associated with each voxel, includes a diffusion rate parameter substantially equal to a convex combination of the eigenvalues of the voxel or to an apparent diffusion coefficient of the voxel.

According to some embodiments of the image processing system, each diffusion ellipsoid corresponding to the first group is displayed in a color scale, corresponding to the magnitude of the diffusion rate parameter.

According to some embodiments of the image processing system, each diffusion ellipsoid corresponding to the second group is displayed in a color from a group consisting of a color not in the color scale and a color at the upper end of the color scale.

According to an aspect of some embodiments, there is provided an MRI scanner. The MRI scanner includes the image processing system specified above. The MRI scanner is configured for diffusion tensor imaging.

Certain embodiments disclosed herein may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

Embodiments of methods and/or devices disclosed herein may involve performing or completing selected tasks manually, automatically, or a combination thereof. Some embodiments are implemented with the use of components that comprise hardware, software, firmware or combinations thereof. According to some embodiments, some components are general-purpose components such as general purpose computers or processors. According to some embodiments, some components are dedicated or custom components such as circuits, integrated circuits or software.

For example, according to some embodiments, some of an embodiment may be implemented as a plurality of software instructions executed by a data processor, for example, which is part of a general-purpose or custom computer. According to some embodiments, the data processor or computer may comprise a volatile memory for storing instructions and/or data, and/or a non-volatile storage, for example, a magnetic hard-disk and/or removable media, for storing instructions and/or data. According to some embodiments, implementation includes a network connection. According to some embodiments, implementation includes a user interface, generally comprising one or more input devices (e.g. allowing input of commands and/or parameters) and output devices (e.g. allowing reporting parameters of operation and results).

BRIEF DESCRIPTION OF THE FIGURES

The patent or application file contains at least one drawing executed in color. Copies of this patent or patent application publication with color drawing(s) will be provided by the Office upon request and payment of the necessary fee.

Some embodiments disclosed herein are described with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the Figures are not drawn to scale.

In the Figures:

Figure 1A:
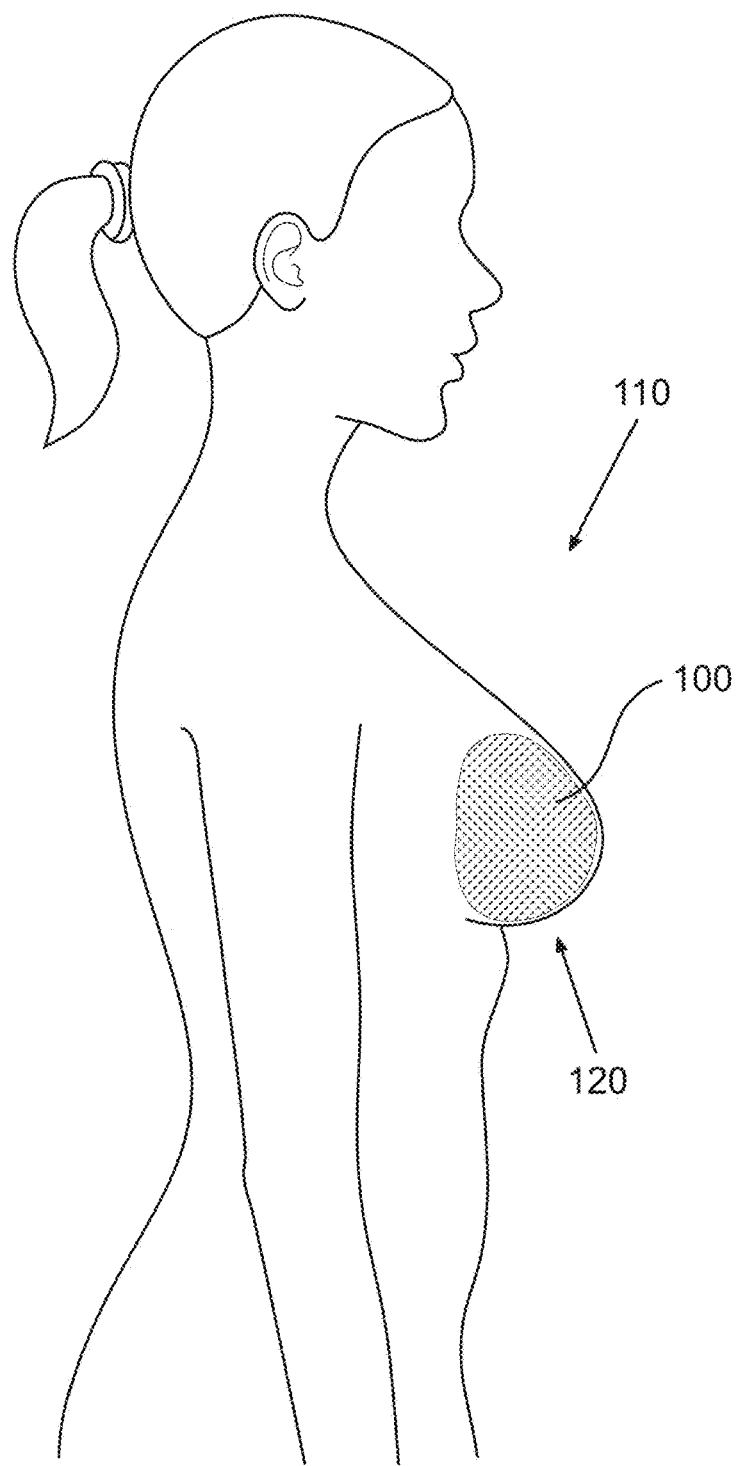
Figure 1B:
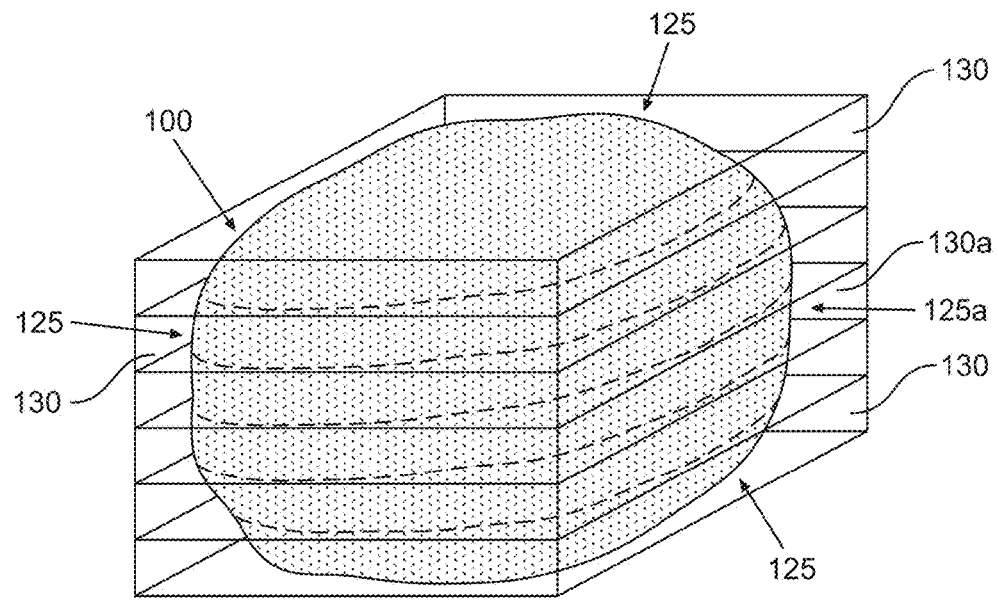
Figure 1C:
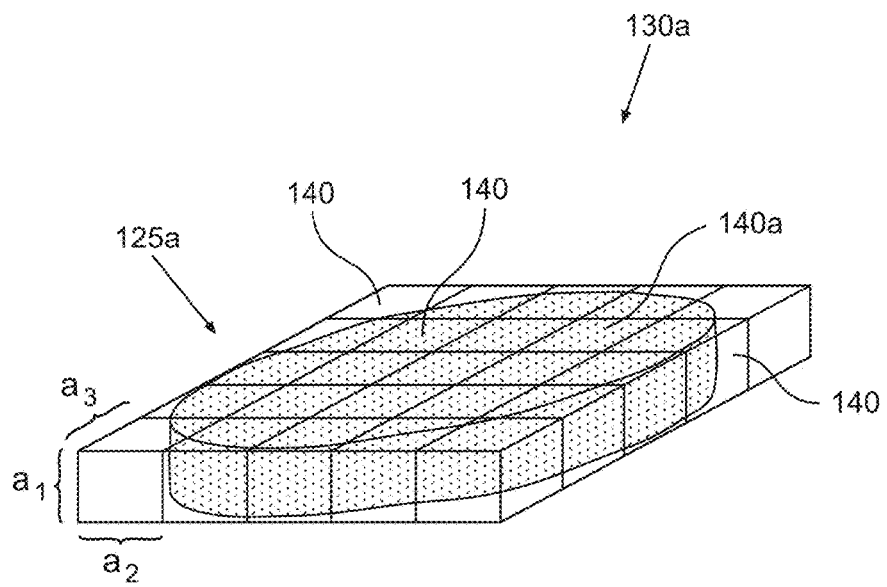
Figure 3:
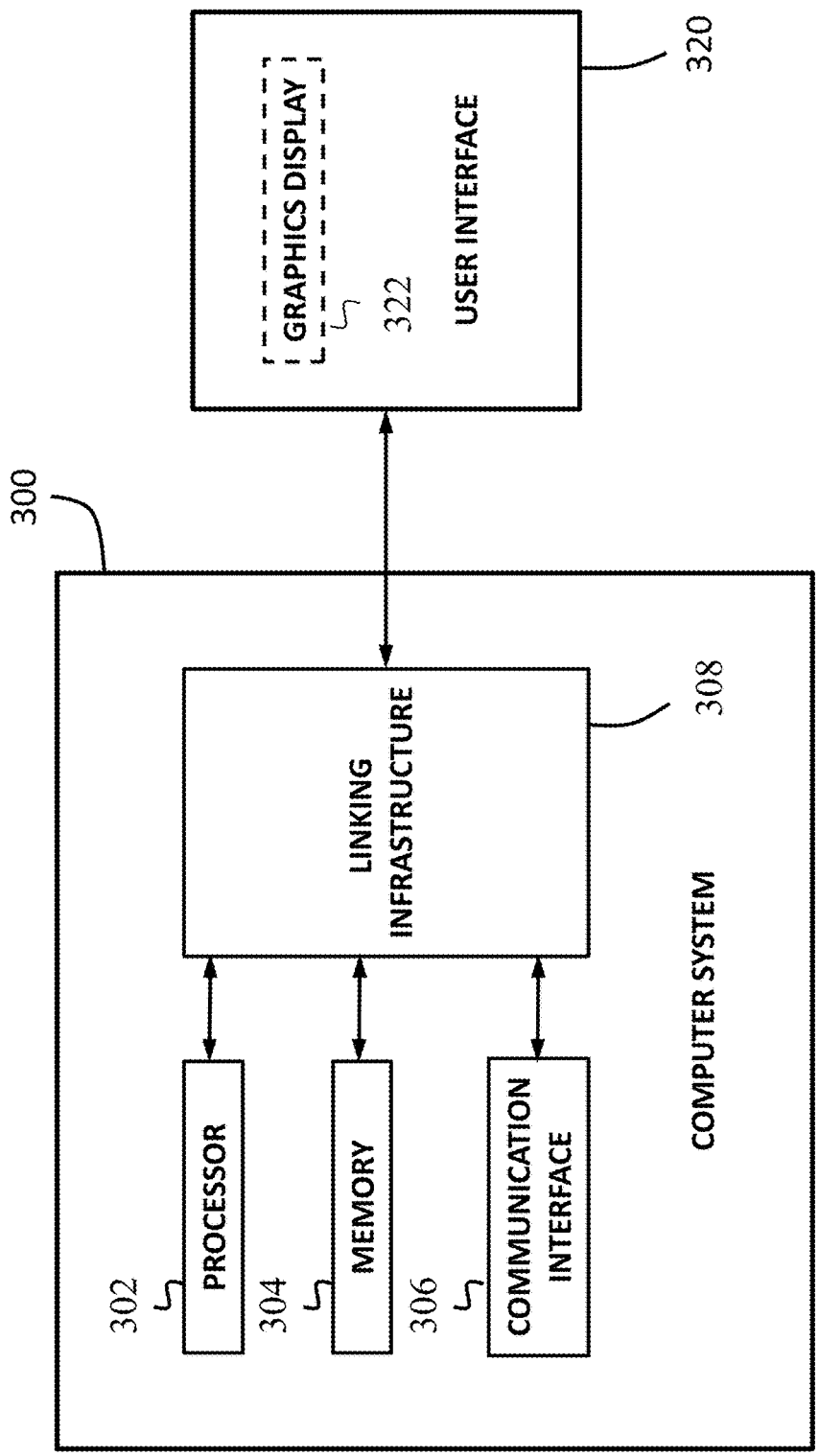
Figure 4:
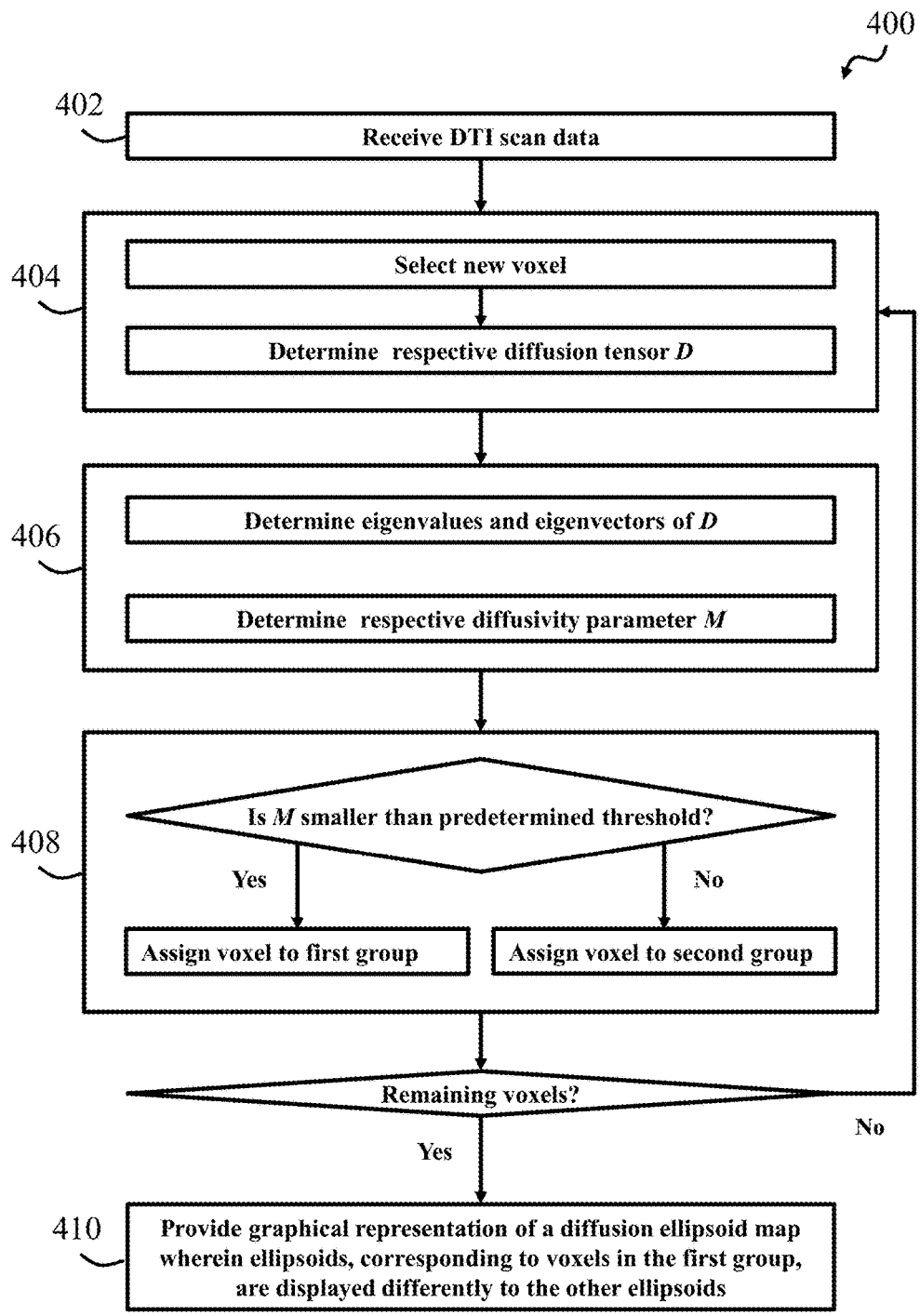
Figure 5A:
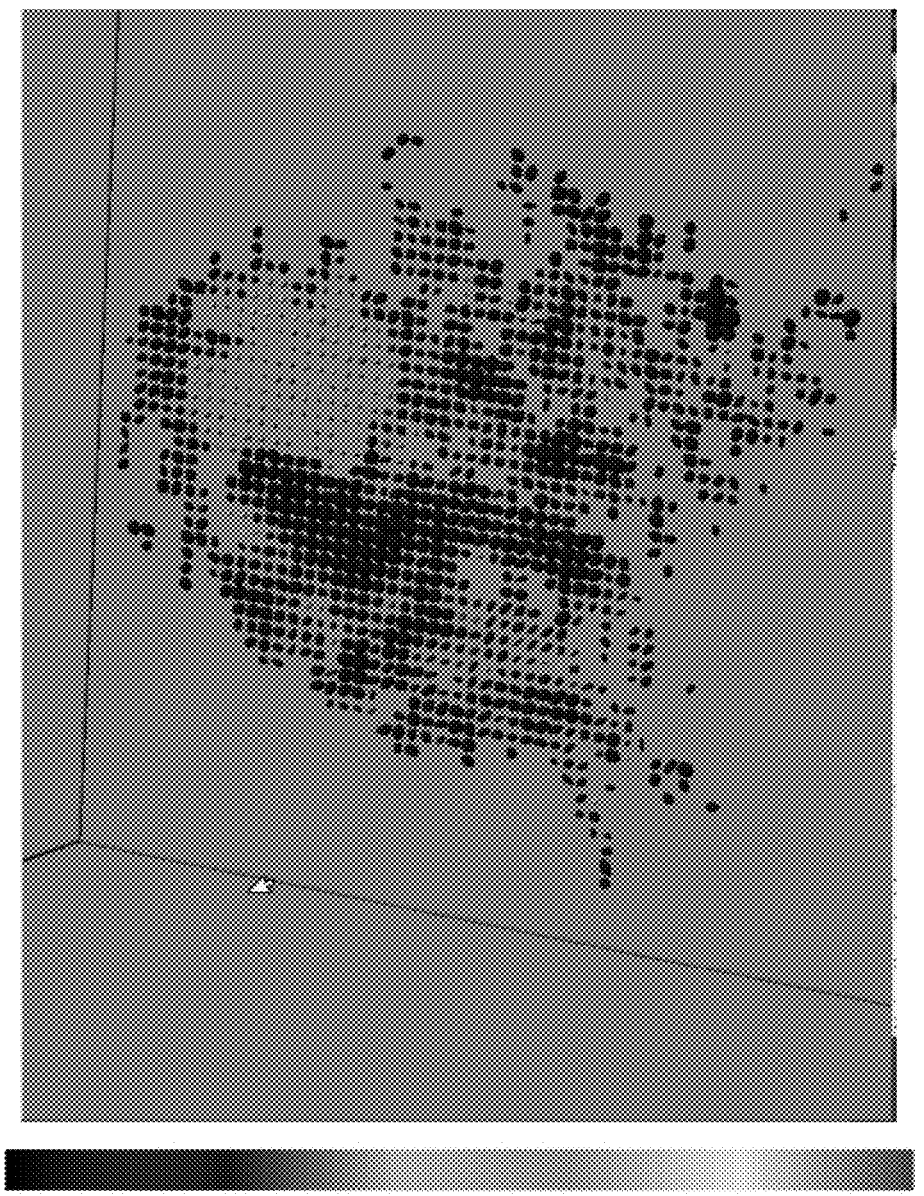
Figure 5B:
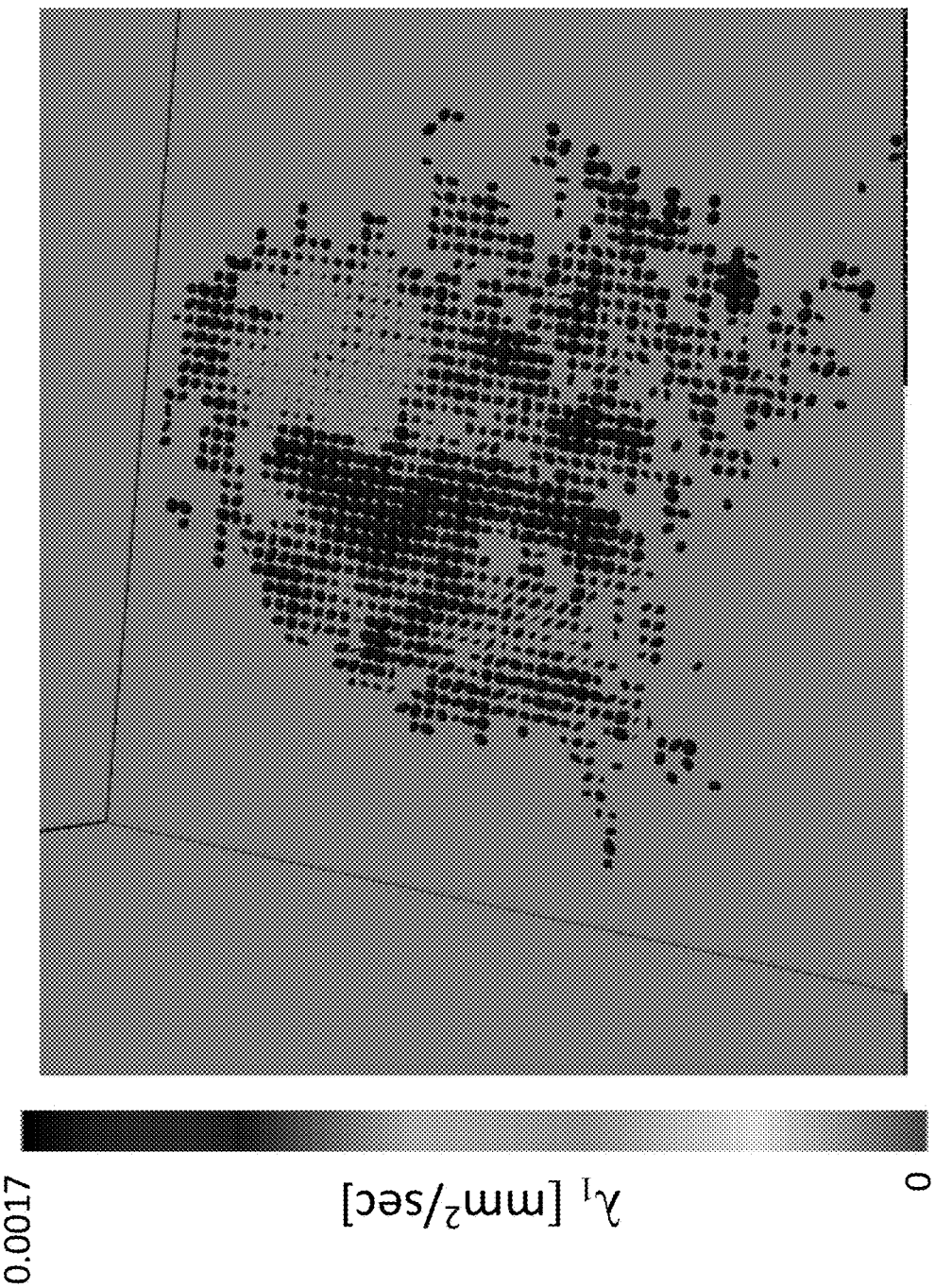
Figure 5C:
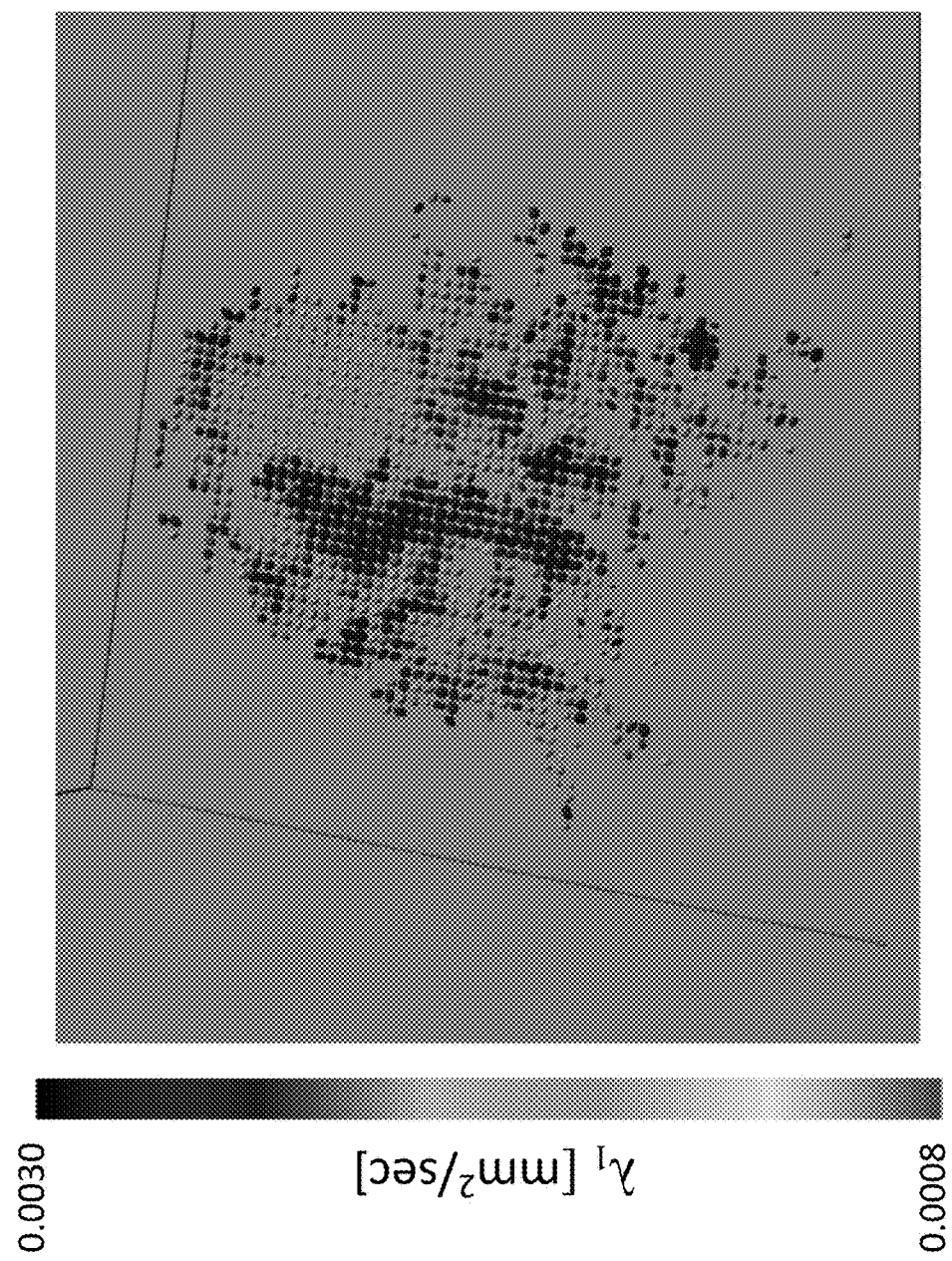
Figure 6A:
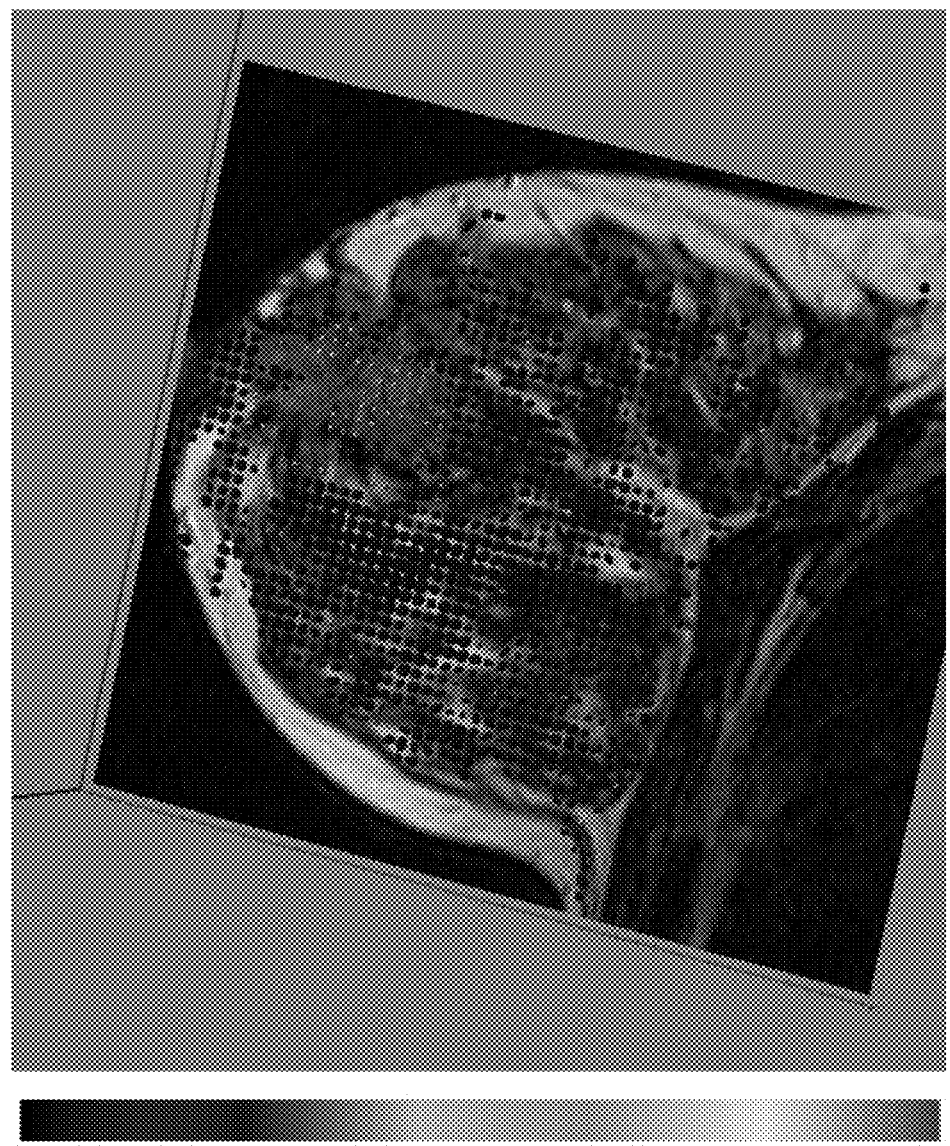
Figure 6B:
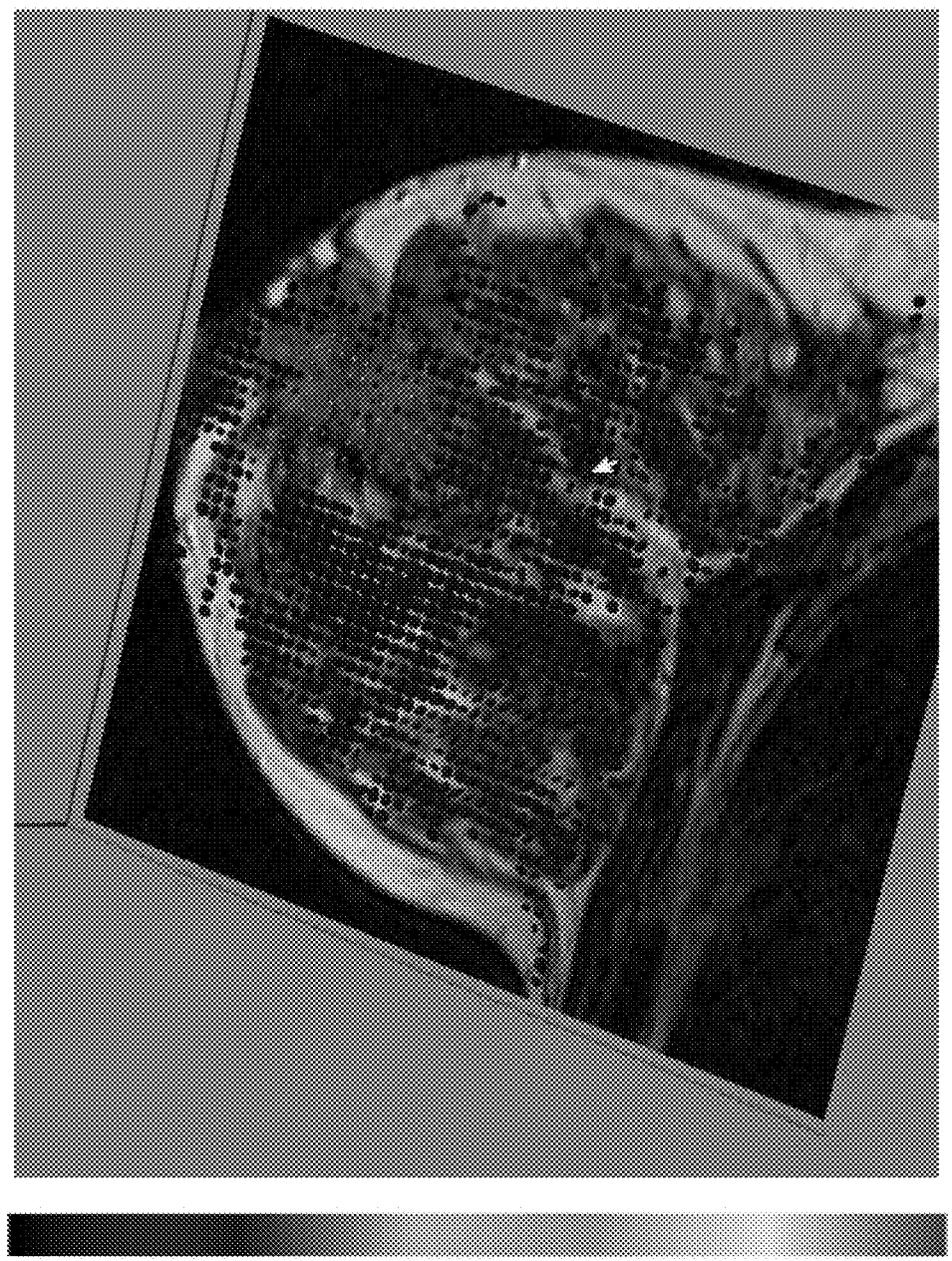
Figure 7A:
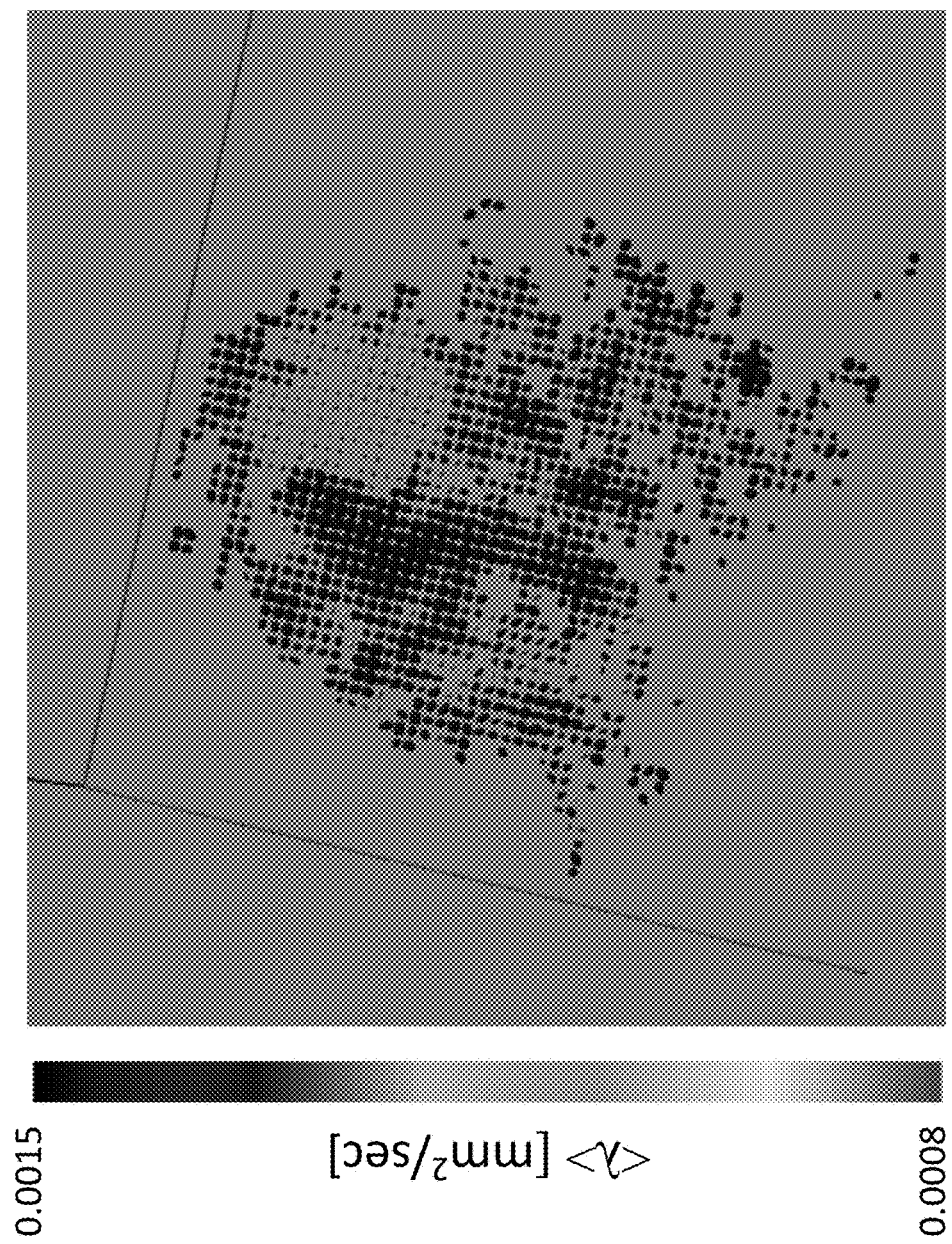
Figure 7B:
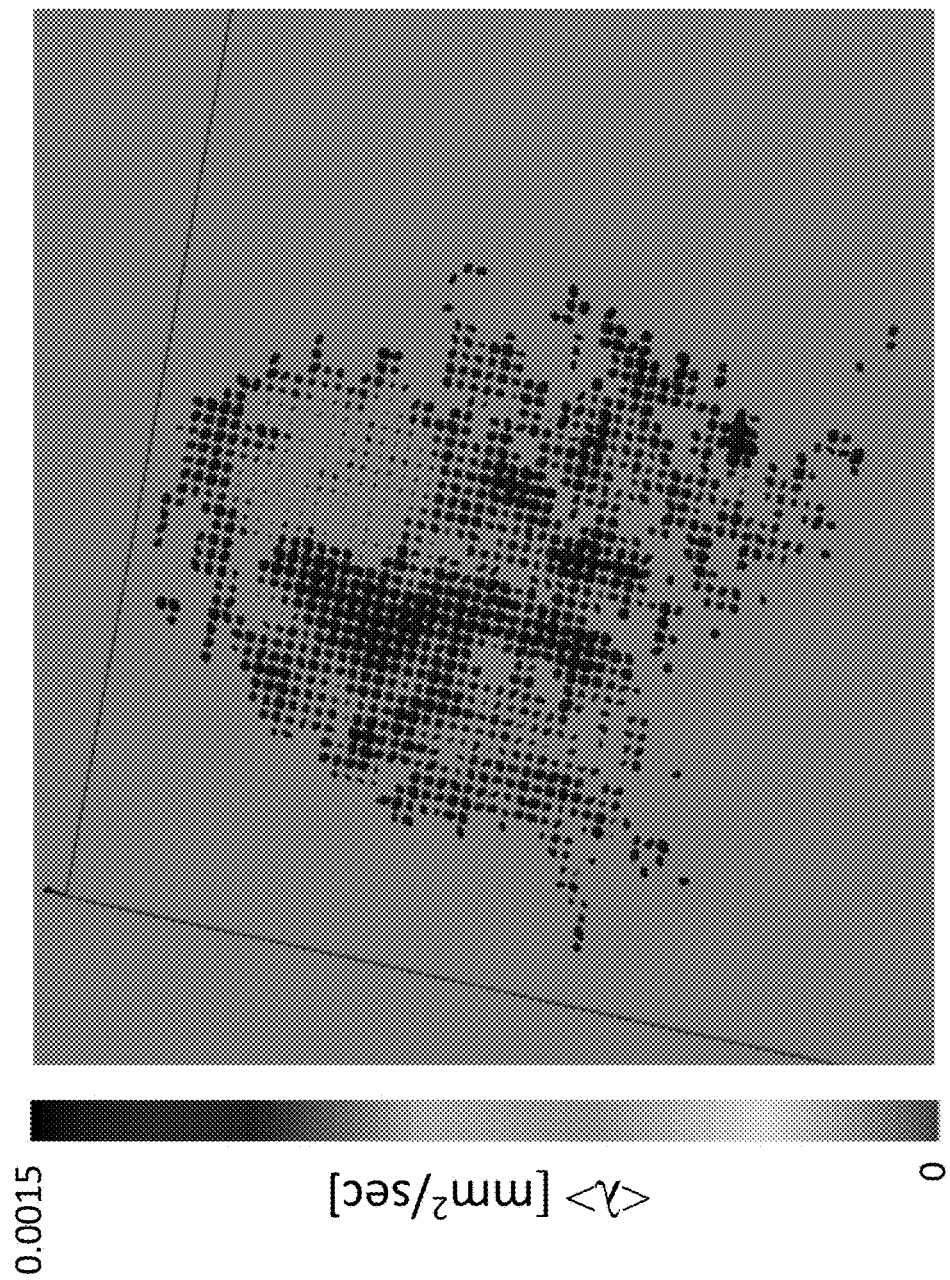
Figure 7C:
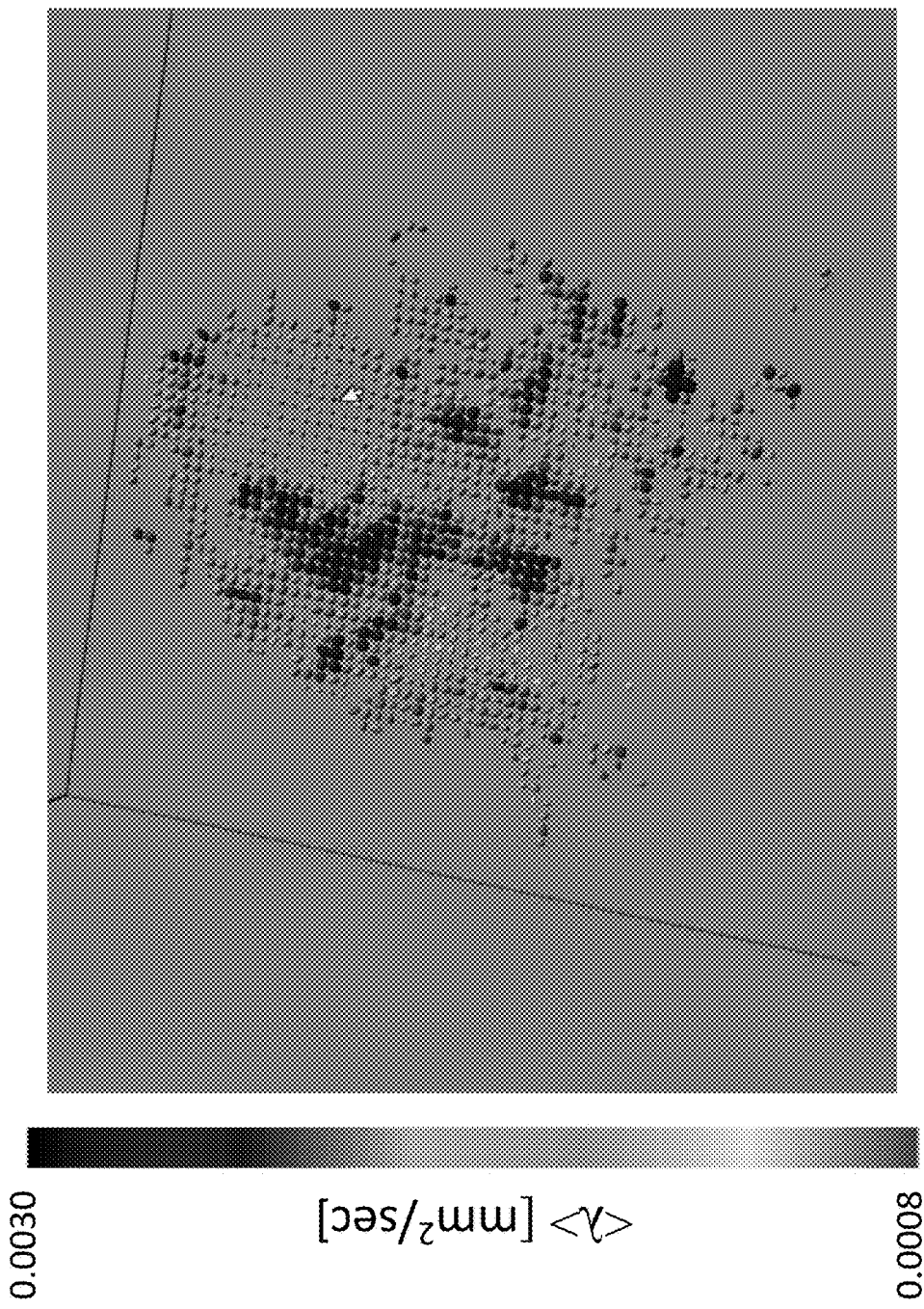
Figure 8:
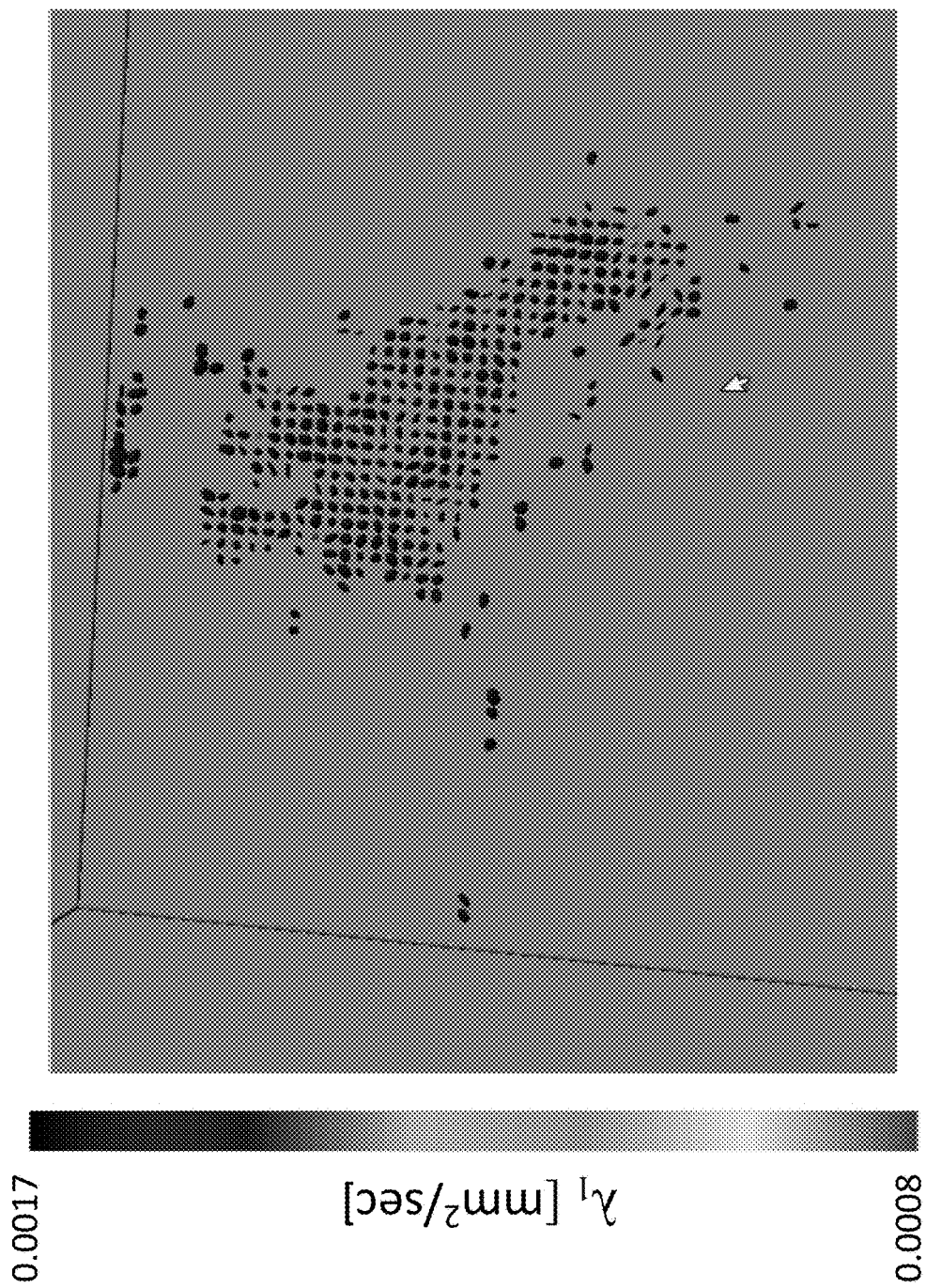
Figure 9:
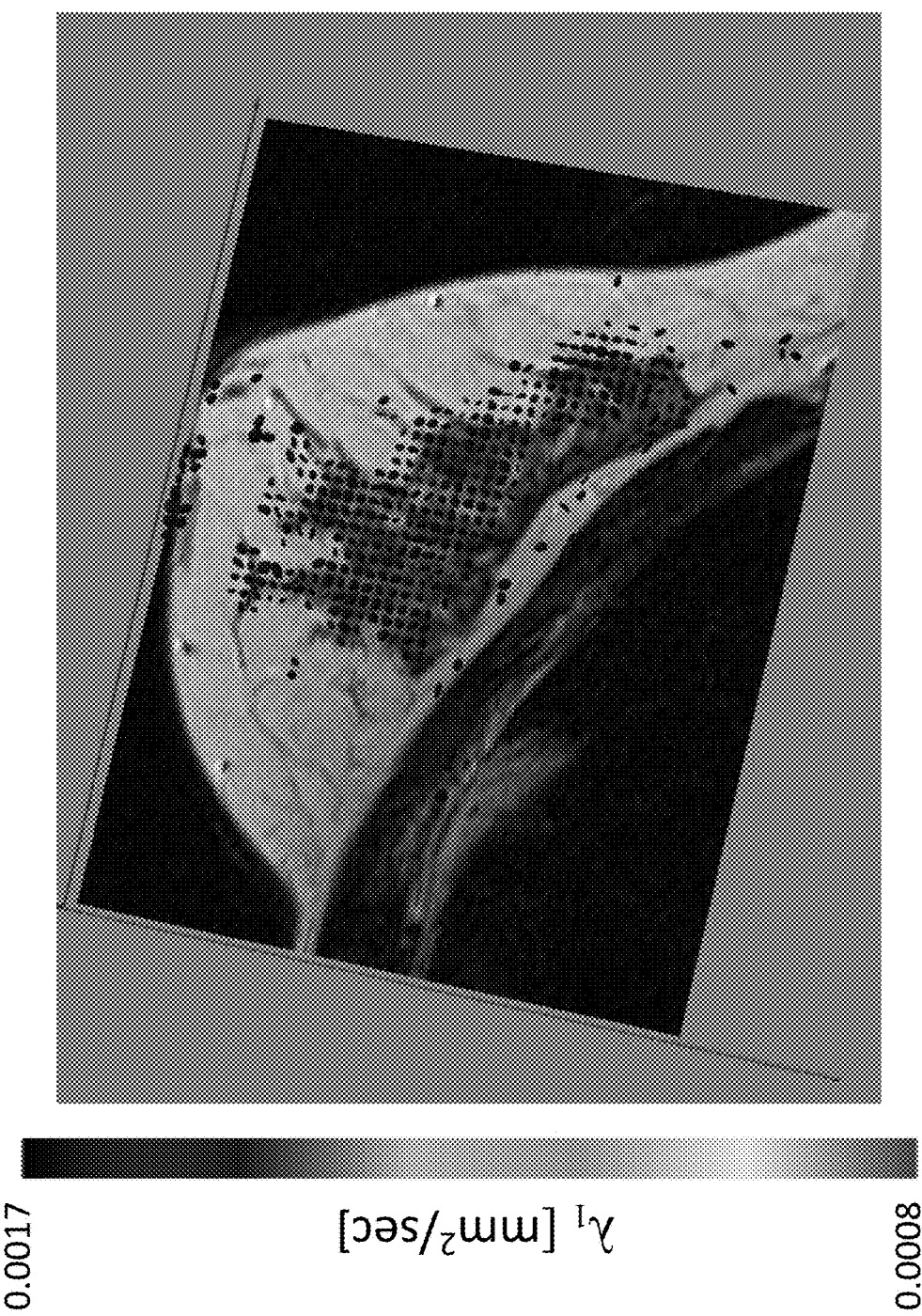
Figure 10:
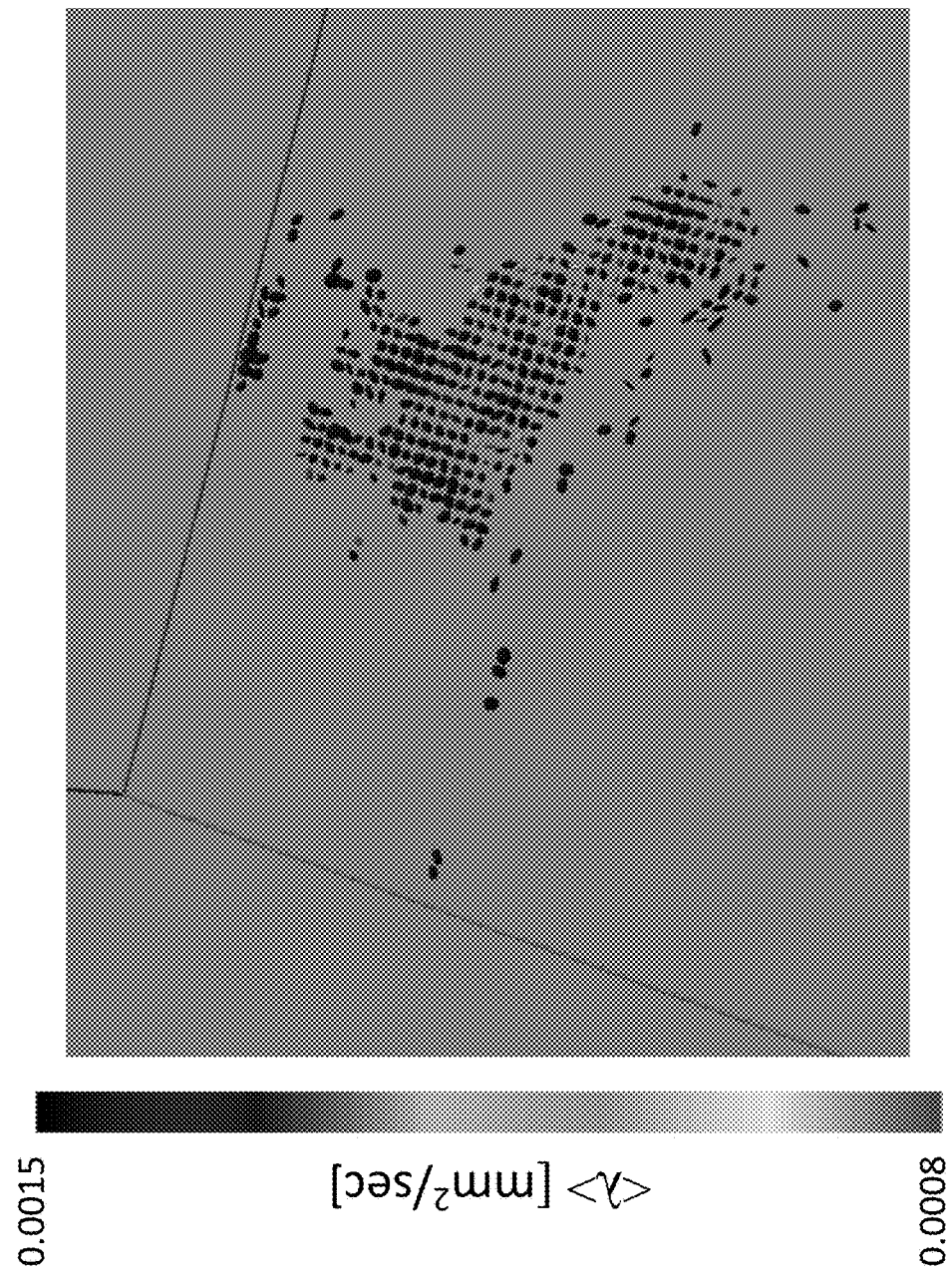
Figure 11:
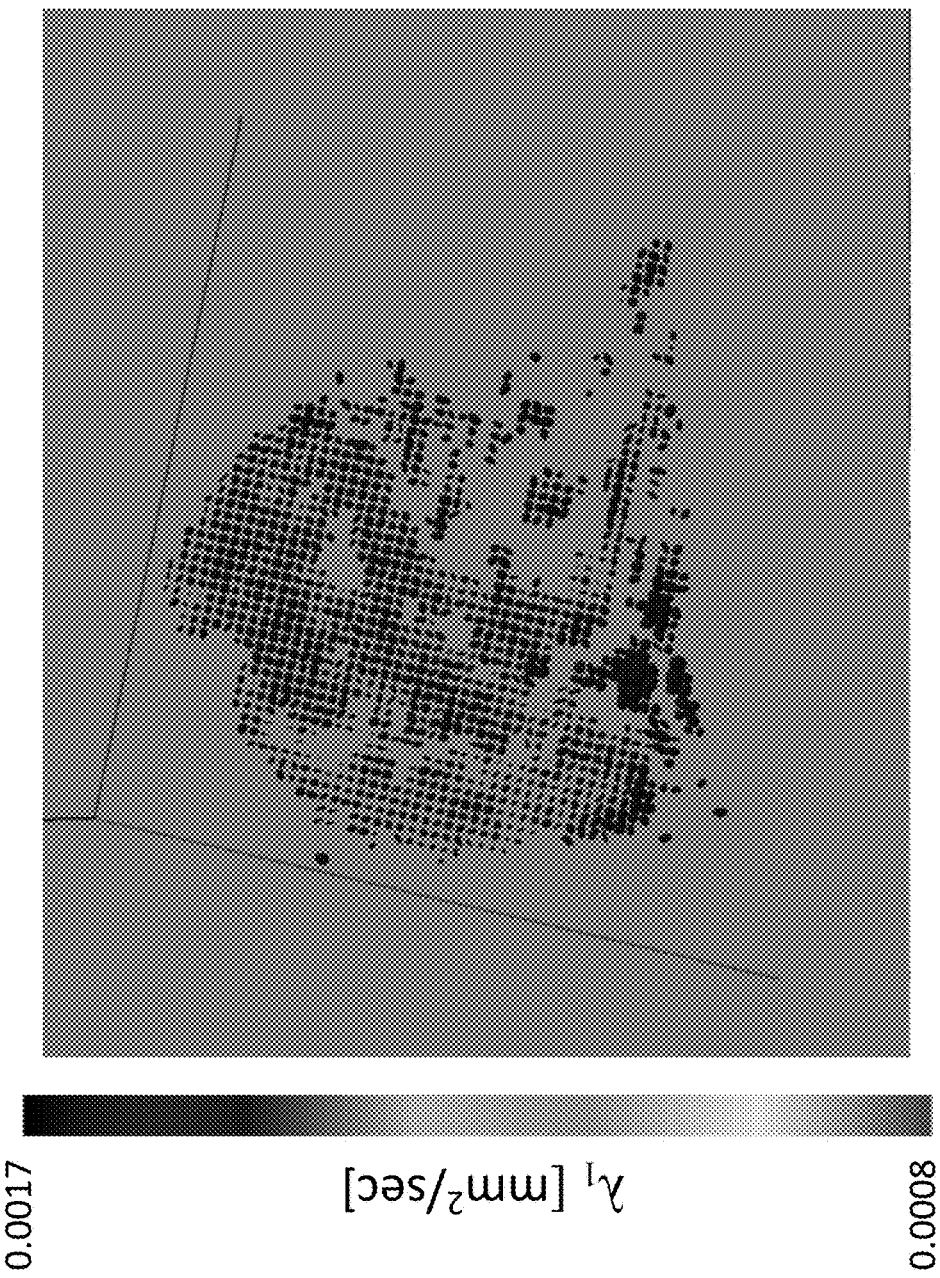
Figure 12:
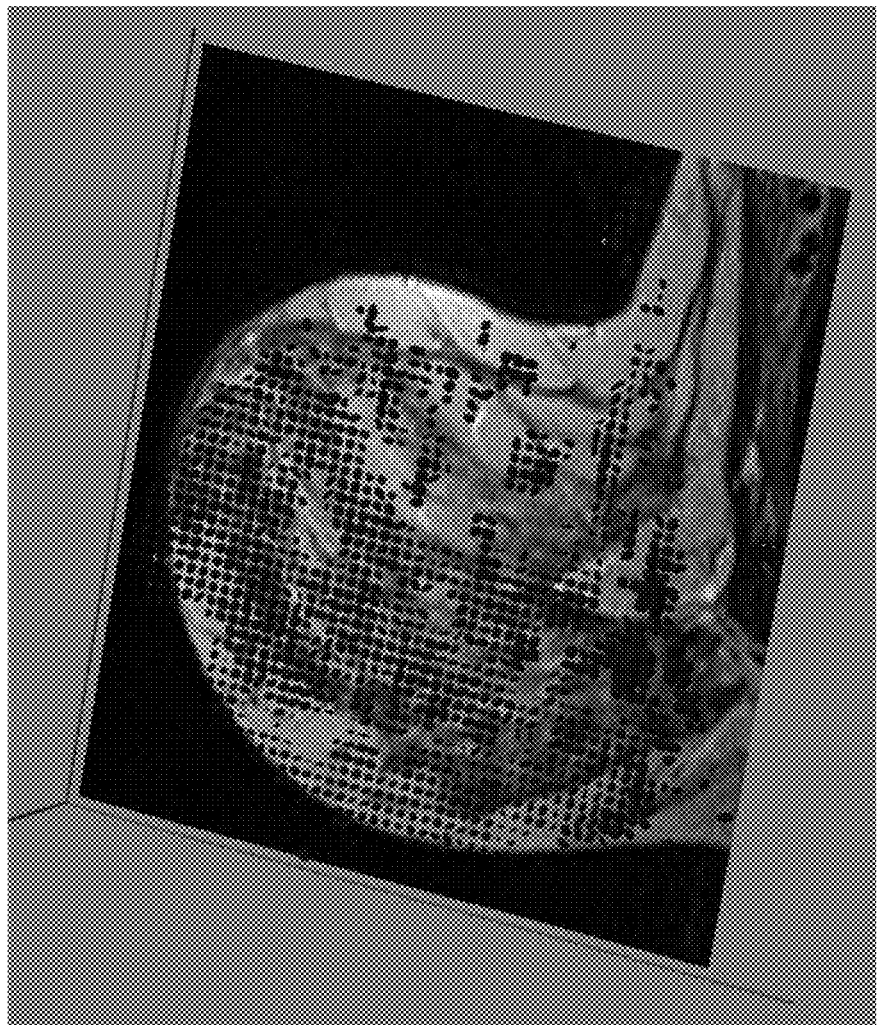
Figure 13:
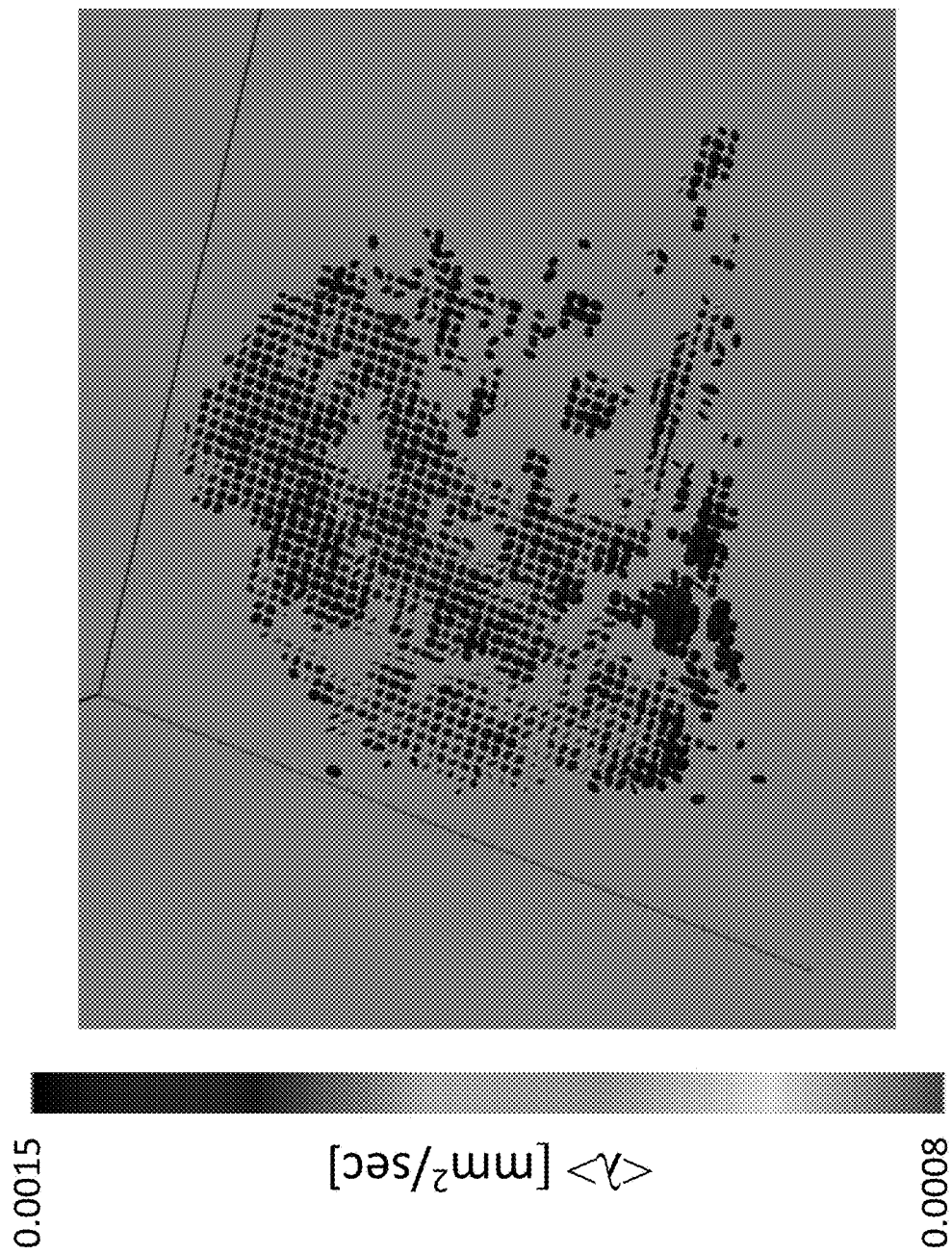
Figure 14:
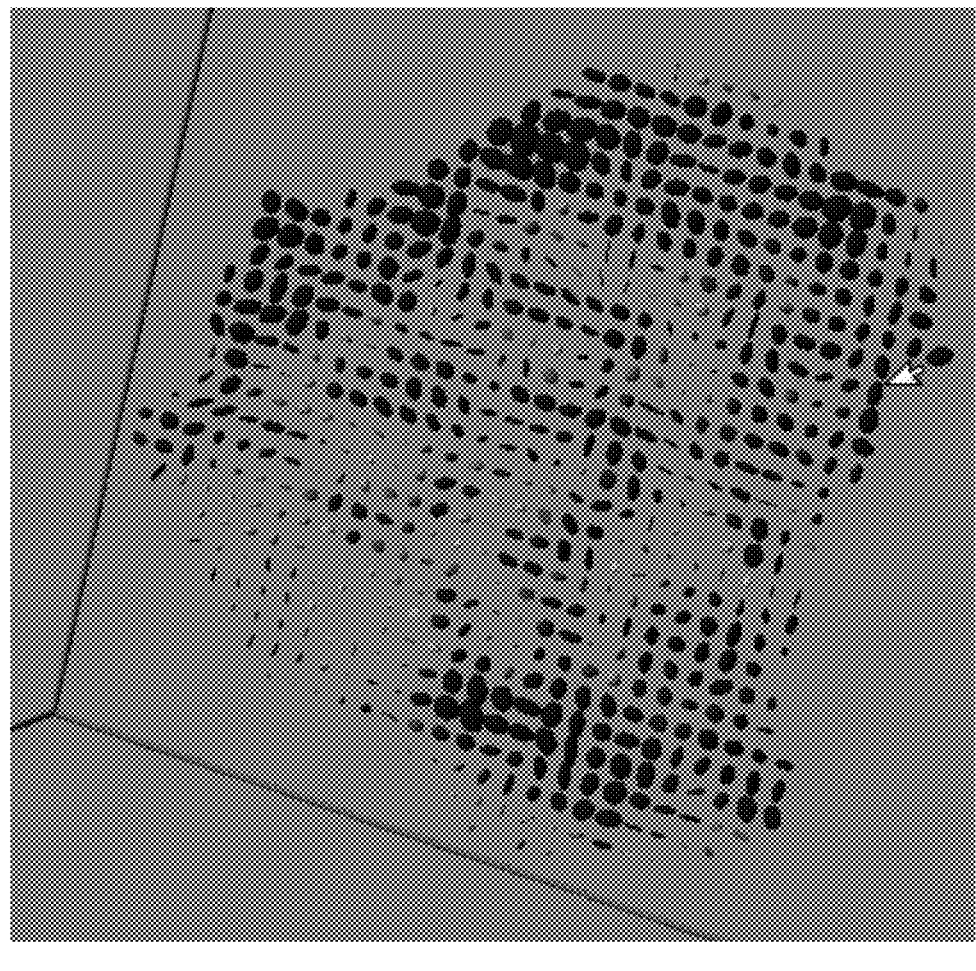
Figure 15:
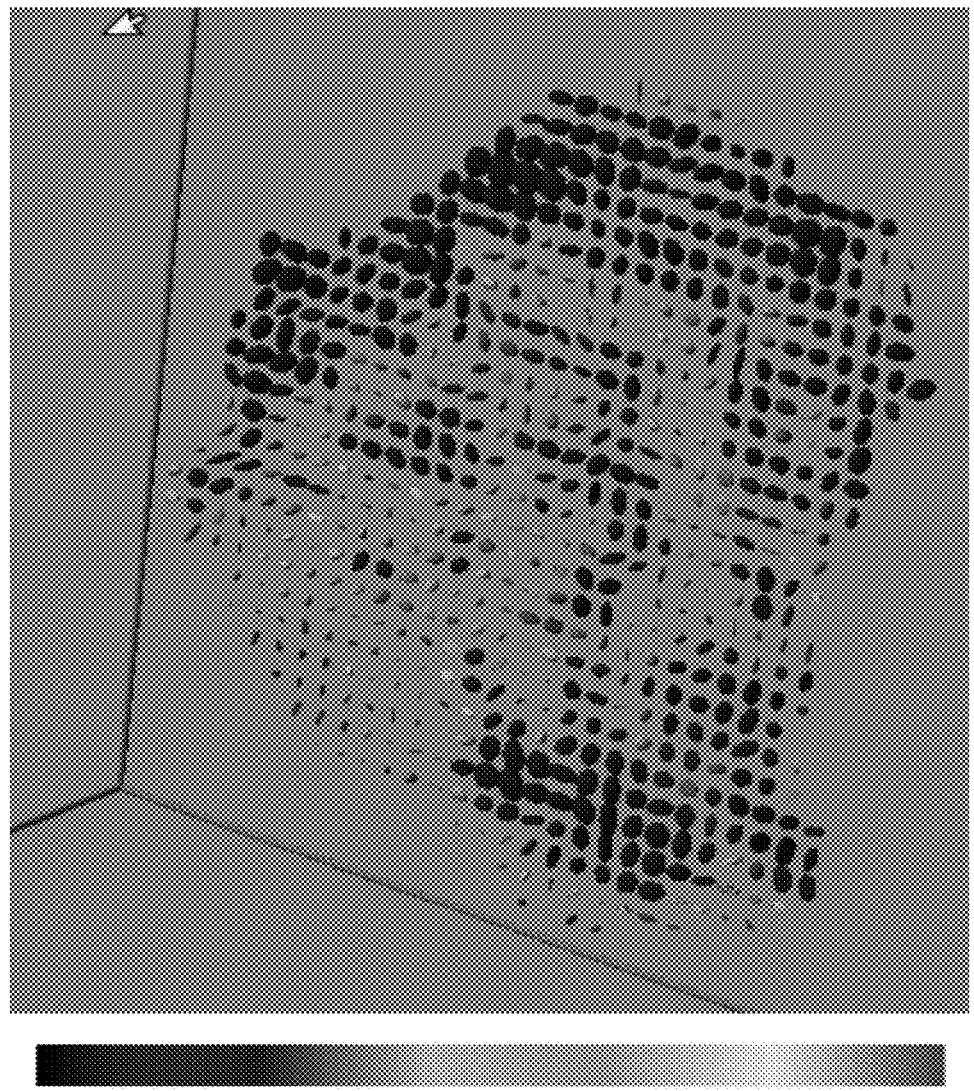
Figure 16:
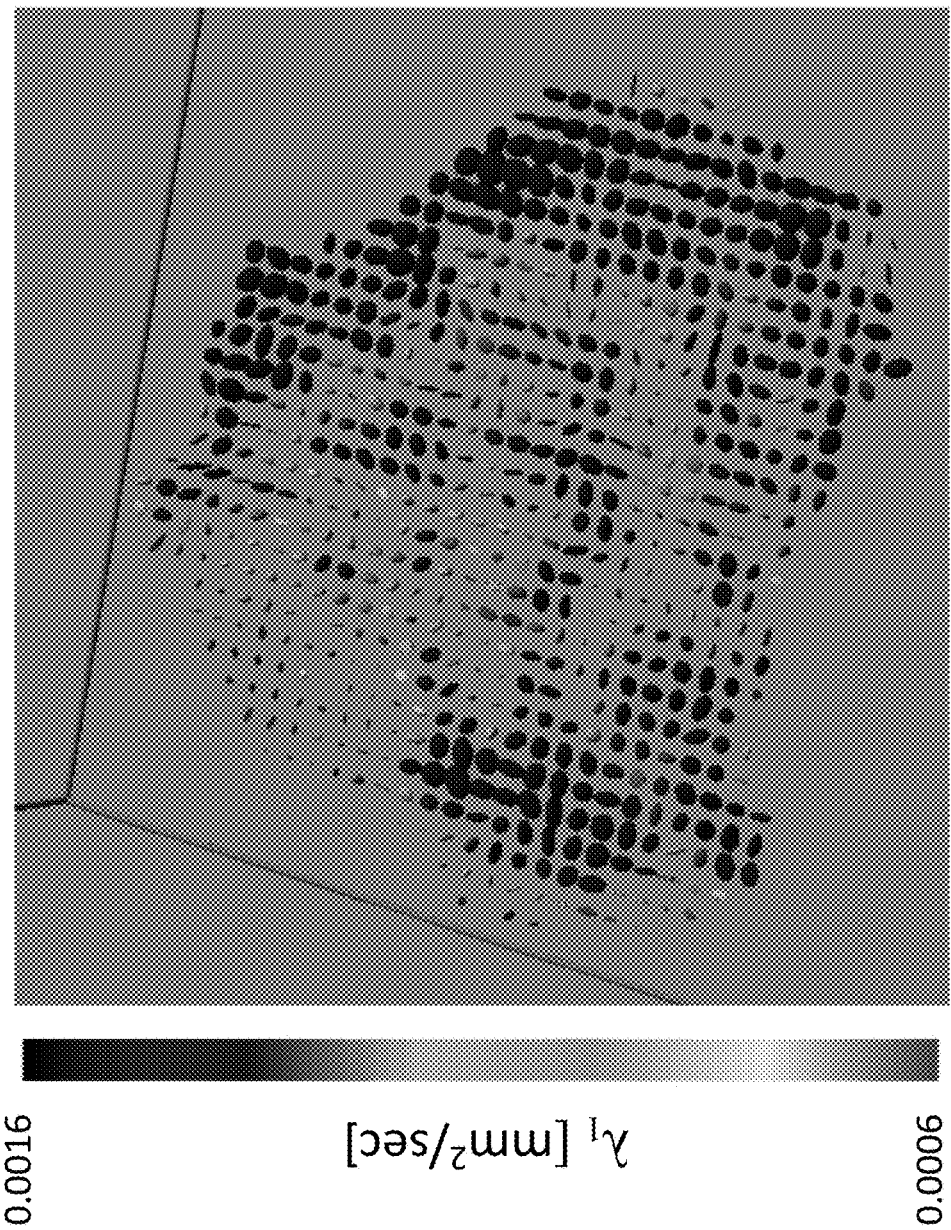
Figure 17:
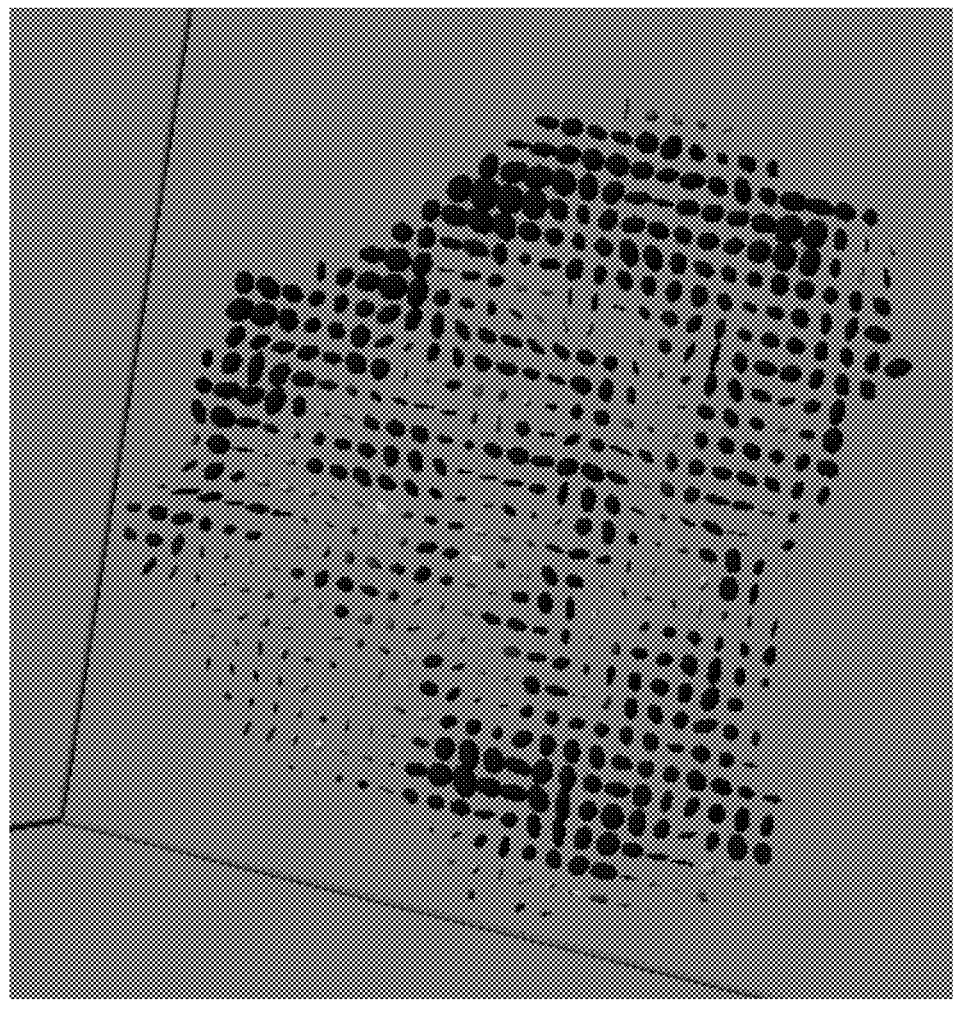
Figure 18:
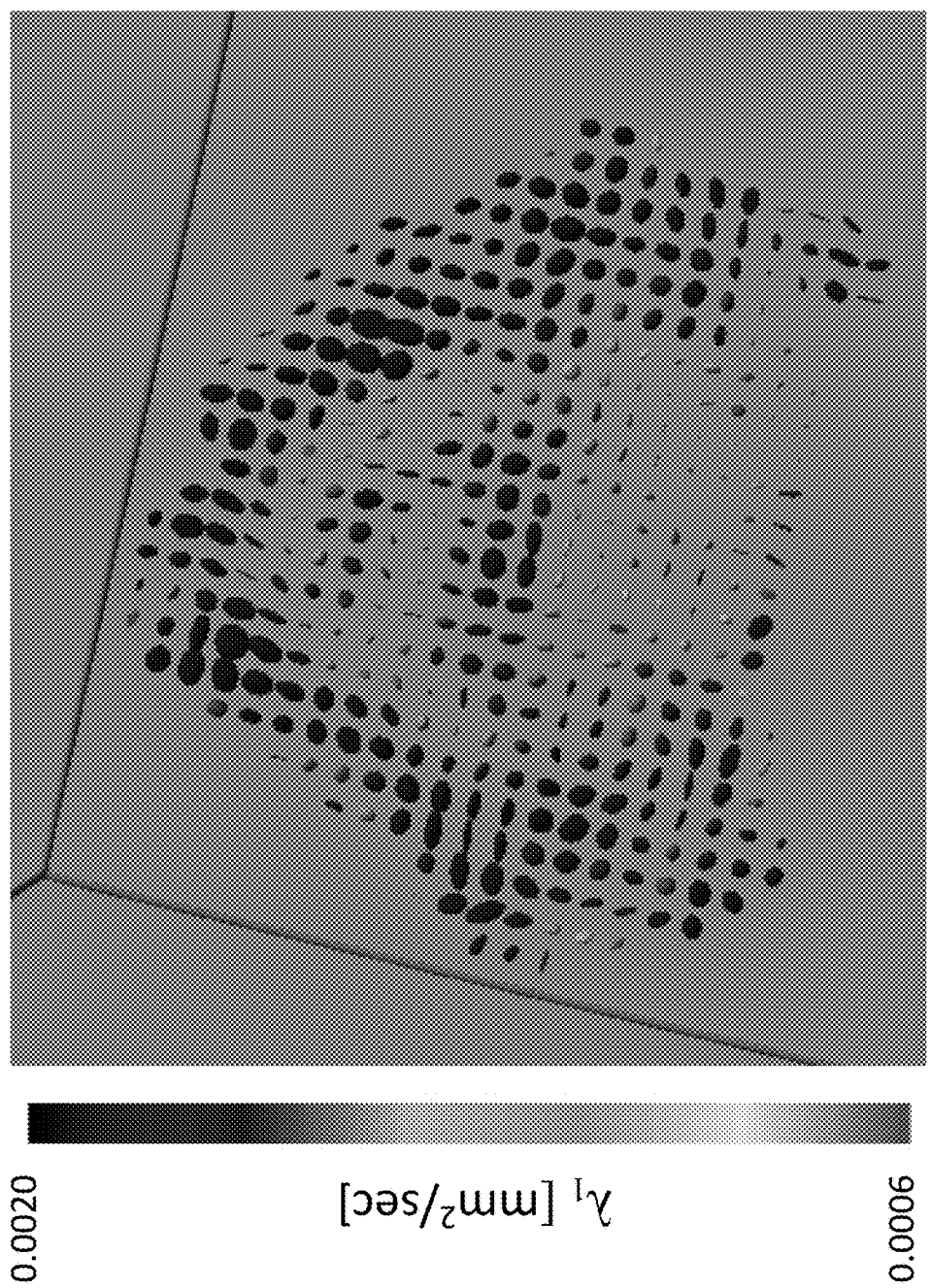
Figure 19:
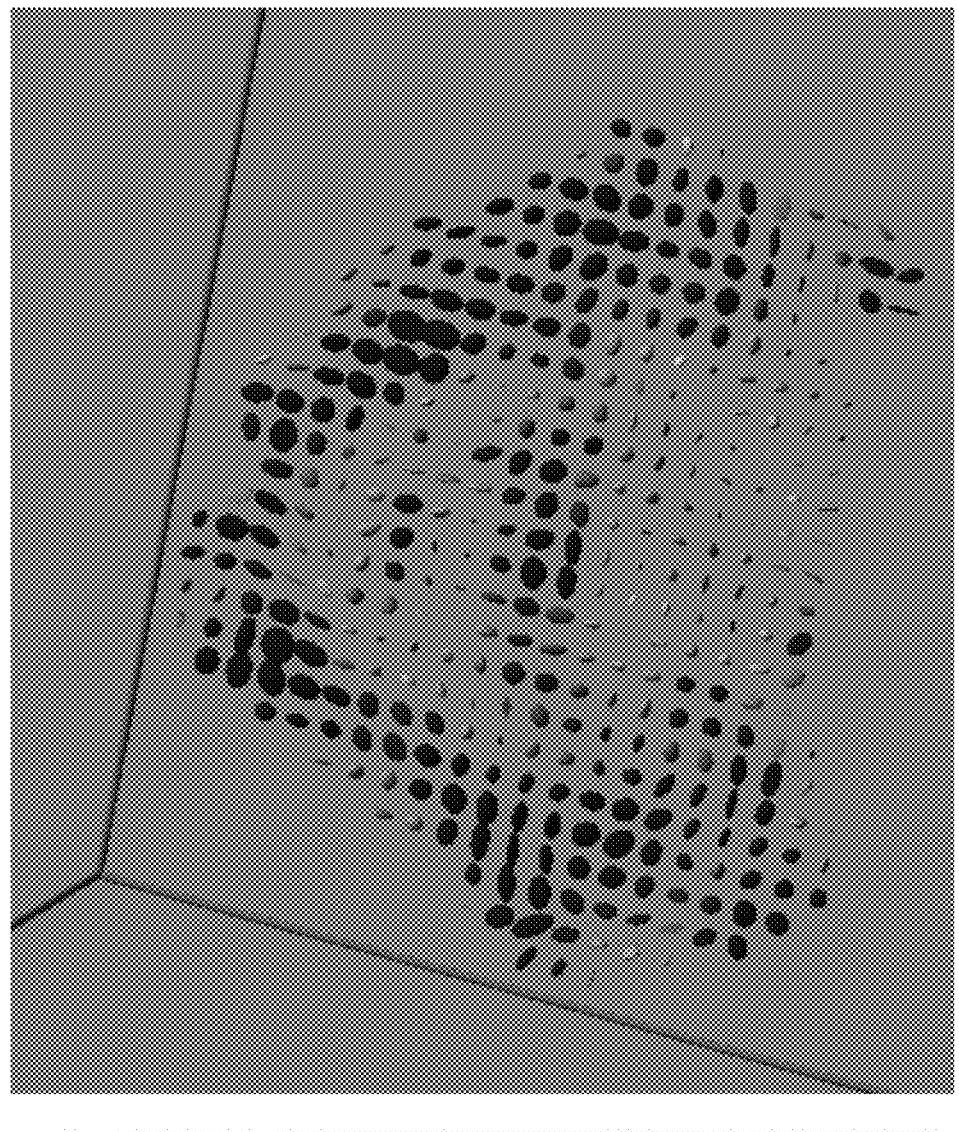

FIG. 1a schematically depicts a subject and a target tissue of the subject, according to some embodiments;

FIG. 1b schematically depicts the target tissue of FIG. 1a, partitioned into slabs, according to some embodiments;

FIG. 1c schematically depicts one of the slabs of FIG. 1b, partitioned into voxels, according to some embodiments;

FIG. 2a schematically depicts a diffusion ellipsoid map of the slab of FIG. 1c, according to some embodiments;

FIG. 2b schematically depicts a diffusion ellipsoid from the diffusion ellipsoid map of FIG. 2a, according to some embodiments;

FIG. 3 schematically depicts a block-diagram of a computer system, which can be employed to generate the diffusion ellipsoid maps disclosed herein, according to some embodiments;

FIG. 4 schematically depicts a flowchart of a diffusion tensor imaging-based method for mapping a target tissue of a subject, according to some embodiments;

FIGS. 5a-5c depict three diffusion ellipsoid maps, respectively, of a slab of a breast with a malignant tumor, colored according to the value of $\lambda_1$, according to some embodiments;

FIGS. 6a-6b depict the diffusion ellipsoid maps of FIGS. 5a-5b, respectively, superimposed on a $T_2$-weighted image of the breast, according to some embodiments;

FIGS. 7a-7c depict three diffusion ellipsoid maps, respectively, of the slab of FIG. 5a, colored according to the value of $\langle\lambda\rangle$, according to some embodiments;

FIG. 8 depicts a diffusion ellipsoid map of a slab of a breast of a subject with a benign tumor, colored according to the value of $\lambda_1$, according to some embodiments;

FIG. 9 depicts the diffusion ellipsoid map of FIG. 8 superimposed on a $T_2$-weighted image of the breast, according to some embodiments;

FIG. 10 depicts a diffusion ellipsoid map of the slab of FIG. 8, colored according to the value of $\langle\lambda\rangle$, according to some embodiments;

FIG. 11 depicts a diffusion ellipsoid map of a slab of healthy breast tissue, colored according to the value of $\lambda_1$, according to some embodiments;

FIG. 12 depicts the diffusion ellipsoid map of FIG. 11 superimposed on a $T_2$-weighted image of the breast, according to some embodiments;

FIG. 13 depicts a diffusion ellipsoid map of the slab of FIG. 11, colored according to the value of $\langle\lambda\rangle$, according to some embodiments;

FIG. 14 depicts a diffusion ellipsoid map of a slab of a prostate with malignant tumors in a peripheral zone and the central zone thereof, colored according to the value of $\lambda_1$, according to some embodiments;

FIG. 15 depicts a diffusion ellipsoid map of the slab of FIG. 14, colored according to the value of $\langle\lambda\rangle$ (ADC), according to some embodiments;

FIG. 16 depicts a diffusion ellipsoid map of the slab of FIG. 14, colored according to the value of $\lambda_1$ with the upper end of the color scale being adapted for detection of cancer in the central zone of the prostate, according to some embodiments;

FIG. 17 depicts a diffusion ellipsoid map of the slab of FIG. 14, colored according to the value of $\langle\lambda\rangle$ with the upper end of the color scale being adapted for detection of cancer in the central zone of the prostate, according to some embodiments;

FIG. 18 depicts a diffusion ellipsoid map of a slab of a prostate with a malignant tumor in a peripheral zone of the prostate, colored according to the value of $\lambda_1$, according to some embodiments; and FIG. 19 depicts a diffusion ellipsoid map of the slab of FIG. 18, colored according to the value of $\langle\lambda\rangle$, according to some embodiments.

DETAILED DESCRIPTION OF SOME EMBODIMENTS

The principles, uses and implementations of the teachings herein may be better understood with reference to the accompanying description and figures. Upon perusal of the description and figures present herein, one skilled in the art is able to implement the teachings herein without undue effort or experimentation. In the Figures, like reference numerals refer to like parts throughout.

Novel Diffusion Ellipsoid Maps

As used herein, the term "about" means approximately, in the region of, roughly, or around. A parameter or quantity is said to be "about", or equal to "about", a numerical value (e.g. $\langle\lambda\rangle$ equals about 0.0015 mm$^2$/sec) when it is within a range, thereby extending the boundaries above and below the numerical values set forth. In general, the term "about" is used herein to modify a numerical value above and below the stated value by a variance of 20%. According to some embodiments, "about" is used herein to modify a numerical value above and below the stated value by a variance of 15%. According to some embodiments, "about" is used herein to modify a numerical value above and below the stated value by a variance of 10%.

As used herein, "set" refers to a collection of one or more elements, e.g. one or more quantities or parameters (such as parameters characterizing diffusion at a spatial coordinate). A set may consist of a single element, e.g. a single parameter (such as a diffusion parameter indicative of a magnitude of the diffusion within a voxel, or a diffusion parameter indicative of an anisotropy or isotropy of the diffusion within the voxel).

As used herein, according to some embodiments, a pair of voxels is "adjacent" when the voxels are neighboring, that is to say, share a facet, at least one edge, or at least one vertex. According to some embodiments, a pair of slabs or a pair of slices is "adjacent" when they share a facet.

FIG. 1a schematically depicts a target tissue 100 of a subject 110. According to some embodiments, subject 110 is female and target tissue 100 corresponds to tissue within a breast 120 of subject 110.

In FIG. 1b target tissue 100 is shown partitioned into slabs 125. Each of slabs 125 is contained within a corresponding, equally thick slice from slices 130. Slices 130 may be equally thick, having a thickness $a_1$. FIG. 1c depicts one of slices 130: a slice 130a (containing a slab 125a from slabs 125). Slice 130a is shown partitioned into voxels 140, that is to say, with a voxel grid overlaid thereon. Each of voxels 140 may be shaped as a cuboid (i.e. a right-angled box) with a height equal to the thickness of slice 130a. For example, a voxel 140a from voxels 140 has a height $a_1$, a width $a_2$, and a depth $a_3$.

The term "voxel", as used herein, generally refers to a cuboid (i.e. a three-dimensional rectangular region) within a slice, preferably a slice containing a slab of a target tissue, in the context of an MRI scan, with dimensions determined by scan parameters of the MRI scan, such as the field-of-view and the number of samples taken per slice, as known in the art.

It is noted that target tissue 100 may be partitioned into slabs in different ways. In FIG. 1b target tissue is shown partitioned into axial slabs, but target tissue 100 may also be partitioned, for example, into slabs perpendicular to slabs 125 (e.g. into coronal slabs) or to slabs obliquely oriented relative to slabs 125, e.g. at 45°.

Anisotropic diffusion requires more than a single parameter for the characterization thereof, being generally characterized by a symmetric, positive diffusion tensor, as follows:

$$D = \begin{pmatrix} D_{xx} & D_{xy} & D_{xz} \\ D_{yx} & D_{yy} & D_{yz} \\ D_{zx} & D_{zy} & D_{zz} \end{pmatrix}$$

where x, y, and z denote coordinates in a Cartesian coordinate system. The diffusion coefficients (the $D_{ij}$), characterizing the diffusion within a voxel in a sample (e.g. a target tissue), are determined by subjecting the sample to sequences of magnetic field gradient pulses (diffusion gradients) in n≥6 non-colinear directions, and measuring the resultant signals (i.e. the resultant magnetic fields). These techniques are staple in the art of DTI and are not repeated here.

FIG. 2a schematically depicts a diffusion ellipsoid map 200 of slice 130a, generated according to some embodiments, as further elaborated on below in the description of FIGS. 3-4. Diffusion ellipsoid map 200 includes diffusion ellipsoids 210. Each of diffusion ellipsoids 210 is associated with a respective voxel from voxels 140, as further elaborated on below.

To facilitate the presentation, diffusion ellipsoid map 200 is shown with a two-dimensional square grid 220 overlaid thereon, but the skilled person will appreciate that square grid 220 is not an essential feature of diffusion ellipsoid map 200. Indeed, in the art, diffusion ellipsoid maps are usually presented without an overlaid grid. Each of grid intersections 230 (that is to say, the grid intersections of grid 220) corresponds to a respective voxel from voxels 140. Each of grid intersections 230 indicates respective map coordinates, which correspond to the centerpoint of the respective voxel.

Each of diffusion ellipsoids 210 is centered about a respective grid intersection from grid intersections 230. The dimensions and the orientation of each of diffusion ellipsoids 210 are determined by the diffusion tensor associated with the voxel corresponding to the respective grid intersection, as is standard in the art. For example, a diffusion ellipsoid 210a (depicted in FIG. 2b) from diffusion ellipsoids 210 is centered about a grid intersection 230a from grid intersections 230, and is associated with voxel 140a. The three orthogonal axes of diffusion ellipsoid 210a are determined by the three eigenvalues, $\lambda_1^{(a)}$, $\lambda_2^{(a)}$, and $\lambda_3^{(a)}$, and the corresponding eigenvectors $v_1^{(a)}$, $v_2^{(a)}$, and $v_3^{(a)}$, respectively, of the diffusion tensor $D_a$ associated with voxel 140a (the bracketed superscript on the eigenvalues and on the eigenvectors indicates the correspondence thereof to voxel 140a). According to some embodiments, a first of the axes points in the direction of $v_1^{(a)}$ and has a magnitude equal to (or proportional to) $\lambda_1^{(a)}$, a second of the axes points in the direction of $v_2^{(a)}$ and has a magnitude equal to (or proportional to) $\lambda_2^{(a)}$, and the third of the axes points in the direction of $v_3^{(a)}$ and has a magnitude equal to (or proportional to) $\lambda_3^{(a)}$, and similarly for all the other ellipsoids. According to some embodiments, the first axis points along $v_1^{(a)}$ and has a magnitude equal to (or proportional to) $\sqrt{\lambda_1^{(a)}}$, the second axis points along $v_2^{(a)}$ and has a magnitude equal to (or proportional to) $\sqrt{\lambda_2^{(a)}}$, and the third axis along $v_3^{(a)}$ and has a magnitude equal to (or proportional to) $\sqrt{\lambda_3^{(a)}}$, and similarly for all the other ellipsoids.

According to some embodiments, the first axis points along $v_1^{(a)}$ and has a magnitude equal to $g_1(\lambda_1^{(a)})$, the second axis points along $v_2^{(a)}$ and has a magnitude equal to $g_2(\lambda_2^{(a)})$, and the third axis points along $v_3^{(a)}$ and has a magnitude equal to $g_3(\lambda_3^{(a)})$, wherein the $g_i(x)$, where i=1, 2, or 3, are each a monotonically increasing function of x, at least for x≥0, and similarly for the other diffusion ellipsoids. According to some embodiments, each of the $g_i(x)$ is a monotonically increasing function of x for 0≤x≤0.0030 (0.0030 mm²/sec approximately equaling the diffusion coefficient of water at body temperature).

As used herein, the term "diffusion ellipsoid" may also refer to three-dimensional shapes which are substantially ellipsoidal. The term "diffusion ellipsoid map" may apply not only to maps displaying exact ellipsoids, but also to maps displaying other three-dimensional shapes, such as, shapes which are substantially ellipsoidal, or, for example, cuboids or cuboids with rounded corners, etc.

In the following, a non-indexed D is used to generally refer to the diffusion tensors associated with any of the voxels 140, for example, when describing features common to all of the diffusion tensors. Similarly, non-superscripted $\lambda_1$, $\lambda_2$, and $\lambda_3$ and non-superscripted $v_1$, $v_2$, and $v_3$ are used to generally refer to the eigenvalues and eigenvectors associated with any of voxels 140. Further, the standard convention that $\lambda_1 \geq \lambda_2 \geq \lambda_3$ is adopted herein.

With each of voxels 140 a respective diffusion parameter M is associated, indicative of a magnitude of the diffusion in the voxel. According to some embodiments, the diffusion parameter equals, or substantially equals, $\lambda_1$. According to some embodiments, the diffusion parameter equals, or substantially equals, the apparent diffusion coefficient (ADC). According to some embodiments, the apparent diffusion coefficient is defined as the mean of the eigenvalues (or the "mean diffusivity"), i.e. ADC=$<\lambda>$=$(\lambda_1+\lambda_2+\lambda_3)/3$. According to some embodiments, the apparent diffusion coefficient may be obtained from any number of gradient directions ≥1, including five or fewer sets of measurements, each set of measurements associated with the application of a magnetic field gradient in a different direction, as known in the art (it is noted that at least six different directions are required to obtain the diffusion tensor D). In particular, the apparent diffusion coefficient may be obtained independently of D. According to some embodiments, the apparent diffusion coefficient may be obtained from a single set of measurements associated with the application of a single magnetic field gradient. According to some embodiments, the apparent diffusion coefficient may be obtained from an average of several directions, even over 30 directions (also termed 'D-average' or Davg), if the fitting is of sufficient quality.

It is noted that sometimes $\lambda_2$ provides a good estimate of $<\lambda>$. According to some embodiments, the diffusion parameter equals, or substantially equals, $\lambda_2$ or $\lambda_3$. According to some embodiments, the diffusion parameter is a convex combination of the eigenvalues, i.e. M=$c_1 \cdot \lambda_1 + c_2 \cdot \lambda_2 + c_3 \cdot \lambda_3$, wherein $c_1+c_2+c_3=1$ and $c_1$, $c_2$, $c_3 \geq 0$. As used herein, the term "diffusion rate parameter" may refer to the diffusion parameter M when M is a convex combination (or a substantially convex combination) of $\lambda_1$, $\lambda_2$, and $\lambda_3$, or when M equals (or substantially equals) the apparent diffusion coefficient.

According to some embodiments, the diffusion parameter M is a monotonically increasing function $f(\lambda_1, \lambda_2, \lambda_3)$ of each of $\lambda_1$, $\lambda_2$, and $\lambda_3$. That is to say, for any pair of diffusion tensors with eigenvalues $\{\|_1, \lambda_2, \lambda_3\}$ and $\{\lambda_1, \lambda_2, \lambda_3\}$, respectively, such that $\mu_1 \geq \lambda_1$: $f(\mu_1, \lambda_2, \lambda_3) \geq f(\lambda_1, \lambda_2, \lambda_3)$. Similarly, for any for any pair of diffusion tensors with eigenvalues $\{\lambda_1, \mu_2, \lambda_3\}$ and $\{\lambda_1, \lambda_2, \lambda_3\}$, respectively, such that $\mu_2 \geq \lambda_2$: $f(\lambda_1, \mu_2, \lambda_3) \geq f(\lambda_1, \lambda_2, \lambda_3)$. And, for any pair of diffusion tensors with eigenvalues $\{\lambda_1, \lambda_2, \mu_3\}$ and $\{\lambda_1, \lambda_2, \lambda_3\}$, respectively, such that $\mu_3 \geq \lambda_3$: $f(\lambda_1, \lambda_2, \mu_3) \geq f(\lambda_1, \lambda_2, \lambda_3)$. According to some embodiments, M is substantially a monotonically increasing function of each of $\lambda_1$, $\lambda_2$, and $\lambda_3$. According to some embodiments, M is a function which monotonically increases, or substantially monotonically increases, with respect to each of $\lambda_1$, $\lambda_2$, and $\lambda_3$ in respective ranges thereof. The respective ranges may be typical of the respective values $\lambda_1$, $\lambda_2$, and $\lambda_3$ assume in human tissue, for example, in breast tissue or prostate tissue. According to some embodiments, wherein the tissue is breast tissue, M is a function which monotonically increases, or substantially monotonically increases, with respect to each of $\lambda_1$, $\lambda_2$, and $\lambda_3$ for $\lambda_1$, $\lambda_2$, $\lambda_3 \leq 0.0030$ mm²/sec—which approximately equals the diffusion coefficient of water at body temperature.

According to some embodiments, ellipsoids associated with voxels whose diffusion parameter is smaller than a threshold K are displayed differently to the other ellipsoids (i.e. ellipsoids associated with voxels for which M≥K). For example, according to some embodiments, ellipsoids associated with voxels whose diffusion parameter M is smaller than the threshold K are colored in a color scale (or a portion of a complete scale of colors), corresponding to the value of M, whereas the other ellipsoids are colored in a single color corresponding to the value of K, and which may be located at an end of the scale (e.g. the top end thereof, as shown, in FIG. 2a). According to some embodiments, the other ellipsoids are colored in a single color which is not included within the color scale. As used herein, two different hues of a same color, e.g. light blue and blue, may be referred to as two different colors. According to some embodiments, ellipsoids associated with voxels whose diffusion parameter M is smaller than K are colored in a first color scale, corresponding to the value of M, whereas the other ellipsoids are colored in a second color scale, which does not overlap with the first color scale. For example, the first color scale and the second color scale may correspond to complementary segments of a third color scale, such that the first color scale corresponds to a bottom half of the third color scale, and the second color scale corresponds to the second (and upper) half of the third color scale. Or, for example, the first color scale may consist of shades of a first color (e.g. light blue to dark blue) and the second color scale may consist of shades of a second color (e.g. light red to dark red) different from the first color. Or, for example, the first color scale may be based on blue and purple, and the second color scale may be based on red and yellow. According to some embodiments, the second color scale also corresponds to the value of M. According to some embodiments, the second color corresponds to the value of K. In some such embodiments, ellipsoids associated with voxels for which M is smaller than K, but is nevertheless very close to K, and the other ellipsoids, may be displayed in different hues/shades of a same color, and thereby distinguished. According to some embodiments, ellipsoids associated with voxels for which M<K are colored in a first color, while the remaining ellipsoids (i.e. ellipsoids associated with voxels for which M≥K) are colored in a second color.

As used herein, the term "color scale" may also refer to a discrete (i.e. non-continuous) color scale. That is to say, a color scale such that with each parameter range in a set of distinct ranges a respective single color is associated. The term "color scale" may also refer to a color scale, which is in part discrete and in part continuous.

According to some embodiments, ellipsoids associated with voxels whose diffusion parameter is smaller than the threshold K are colored differently to the other ellipsoids, while ellipsoids associated with voxels whose diffusion parameter is further smaller than a lower threshold K', K' being smaller than K (i.e. K'<K), are colored in a single color. For example, ellipsoids, associated with voxels for which K'≤M<K, are colored in a color scale corresponding to the value of M, while ellipsoids, associated voxels for which M<K', are colored in a single color, corresponding to the value of K' (while ellipsoids associated with voxels for which M≥K may be colored in a single color corresponding to the value of K). That is to say, ellipsoids associated with voxels for which M<K', are colored in a color at the bottom end of the color scale (while ellipsoids associated with voxels for which M≥K may be colored in a color at the top end of the color scale). A schematic depiction of such a coloring scheme is given in FIG. 2a, wherein diffusion ellipsoids associated with voxels for which M≤K are located inside a first closed curve 260. Diffusion ellipsoids associated with voxels for which M<K' are located inside a second closed curve 270. According to some embodiments, the target tissue is breast tissue, M is, for example, $\lambda_1$, and K' equals about 0.0008 mm$^2$/sec. According to some embodiments, the target tissue is breast tissue, M is $\lambda_1$, K' is about 0.0008 mm$^2$/sec, and K is about 0.0017 mm$^2$/sec. According to some embodiments, the target tissue is peripheral prostate tissue, M is $\lambda_1$, K' is about 0.0006 mm$^2$/sec, and K is about 0.0020 mm$^2$/sec. According to some embodiments, ellipsoids associated with voxels for which M<K' are colored in a first color, ellipsoids associated with voxels for which K'≤M<K are colored in a second color, while the remaining ellipsoids (i.e. ellipsoids associated with voxels for which M≥K) are colored in a third color.

According to some embodiments, ellipsoids associated with voxels, whose respective diffusion parameter M is smaller than the threshold K, are colored according to the orientation of the largest principal axis of the respective diffusion tensor (that is to say, according to $v_1$). For example, if the largest principal axis of an ellipsoid (having a value of M smaller than K) is closest to the x-axis, y-axis or z-axis (of a laboratory, Cartesian frame of reference), the ellipsoid is colored in blue, red, or green, respectively, whereas ellipsoids, having a value of M greater than, or equal to, K, are colored in yellow. Or, for example, an ellipsoid having a value of M smaller than K is colored in a combination of blue, red, and green, weighted according to the proximity of the largest principal axis to each of the respective axes of the laboratory frame, whereas ellipsoids, having a value of M greater than, or equal to, K, are colored in yellow.

According to some embodiments, e.g. wherein the target tissue is breast tissue, with each of voxels 140 a respective second diffusion parameter is associated: a respective anisotropy parameter A, which is indicative of anisotropy of the diffusion within the voxel. According to some embodiments, the anisotropy parameter A equals, or substantially equals, $\lambda_1 - \lambda_3$ (wherein according to the convention adopted herein $\lambda_1 - \lambda_3 \geq 0$). According to some embodiments, the anisotropy parameter A equals, or substantially equals, the fractional anisotropy (FA), the relative anisotropy (RA), or 1-VR, wherein VR is the volumetric ratio (see, for example, Furman-Haran et al., 2016, ibid. for definitions thereof). According to some embodiments, diffusion ellipsoids associated with voxels whose anisotropy parameter A is smaller than an anisotropy threshold B, are displayed differently to the other diffusion ellipsoids. According to some embodiments, diffusion ellipsoids associated with voxels whose diffusion parameter M is smaller than the threshold K, and whose anisotropy parameter A is smaller than the anisotropy threshold B, are displayed differently to the other diffusion ellipsoids. For example, according to some embodiments, diffusion ellipsoids associated with voxels whose diffusion parameter M and anisotropy parameter A are smaller than the threshold K and the anisotropy threshold B, respectively, are colored in the color scale, while the other ellipsoids are colored in one or more colors not in the color scale or at the upper end of the color scale. According to some embodiments, ellipsoids associated with voxels whose respective M is smaller than K and whose respective A is greater than (or equal to) B are also colored differently to the rest of the ellipsoids.

According to some embodiments, e.g. wherein the target tissue is prostate tissue, with each of voxels 140 a respective second diffusion parameter is associated: a respective isotropy parameter I, which is indicative of isotropy of the diffusion within the voxel. According to some embodiments, the isotropy parameter I equals, or substantially equals, 1-FA, 1-RA, or VR. According to some embodiments, diffusion ellipsoids associated with voxels whose isotropy parameter I is smaller than an isotropy threshold J, are displayed differently to the other diffusion ellipsoids. According to some embodiments, diffusion ellipsoids associated with voxels whose diffusion parameter M is smaller than the threshold K, and whose isotropy parameter I is smaller than the isotropy threshold J, are displayed differently to the other diffusion ellipsoids. For example, according to some embodiments, diffusion ellipsoids associated with voxels whose diffusion parameter M and isotropy parameter I are smaller than the threshold K and the isotropy threshold J, respectively, are colored in the color scale, while the other ellipsoids are colored in one or more colors not in the color scale or at the upper end of the color scale. According to some embodiments, ellipsoids associated with voxels whose respective M is smaller than K and whose respective I is greater than (or equal to) J are also colored differently to the rest of the ellipsoids.

According to some embodiments, diffusion ellipsoids 210 are colored according to a color scale 250 as elaborated on below.

In the following, a subscript may be used to indicate the diffusion parameter corresponding to a respective threshold.

Thus, for example, the threshold K corresponding to $\lambda_1$ (i.e. when M=$\lambda_1$) will be denoted as $K_{\lambda_1}$ (which, as mentioned above, equals about 0.0017 mm²/sec for malignant breast tumors, but will generally equal other values for other types of cancer in different body parts), and the threshold corresponding to $\langle\lambda\rangle$ will be denoted as $K_{\langle\lambda\rangle}$. Similarly, the lower threshold K' corresponding to, for example, $\lambda_1$, may be denoted as $K_{\lambda_1}'$, and so on. Similarly, a subscript, indicating the anisotropy parameter corresponding to a respective anisotropy threshold, may be used. Thus, for example, the anisotropy threshold B corresponding to $\lambda_1$-$\lambda_3$ will be denoted as $B_{\lambda_1-\lambda_3}$, and the anisotropy threshold corresponding to FA will be denoted as $B_{FA}$.

Similarly, a subscript, indicating the isotropy parameter corresponding to a respective isotropy threshold, may be used. Thus, for example, the isotropy threshold J corresponding to 1-FA will be denoted as $J_{1-FA}$. According to some embodiments, a voxel having a value of M which is lower than K, indicates the presence of cancer cells within the voxel.

According to some embodiments, values of M lower than K in each voxel within a group of voxels, such that the group includes, for example, three subgroups of voxels in three adjacent slabs, is indicative of a presence of cancer cells within the group when the following conditions are satisfied: (i) The first subgroup of voxels, which consists of voxels in the first slab wherein the first slab is the middle slab, includes at least two adjacent voxels (e.g. four adjacent voxels). (ii) The second subgroup of voxels, which consists of voxels in the second slab, includes at least two voxels which are adjacent to said at least two adjacent voxels in the first subgroup of voxels. (iii) The third subgroup of voxels, which consists of voxels in the third slab, includes at least two voxels, which are adjacent to said at least two adjacent voxels in the first subgroup of voxels.

According to some embodiments, wherein the target tissue is breast tissue, a diffusion ellipsoid map of the target tissue is generated. In the map, diffusion ellipsoids with $\lambda_1$ values lower than $K_{\lambda_1}$, wherein $K_{\lambda_1}$ equals about 0.0017 mm²/sec, are displayed differently to the other diffusion ellipsoids. In particular, diffusion ellipsoids, respectively associated with voxels in a group of voxels, such as the group described above which includes adjacent voxels, are displayed differently to diffusion ellipsoids with $\lambda_1$ values greater than $K_{\lambda_1}$. The map thereby indicates a potential presence of cancer cells within the group of voxels. According to some embodiments, wherein the target tissue is breast tissue, a value of $\lambda_1$ lower than about 0.0017 mm²/sec, in a voxel, indicates a presence of cancer cells within the voxel.

According to some embodiments, wherein the target tissue is breast tissue, M=$\lambda_1$, and A=$\lambda_1$-$\lambda_3$, and wherein in each of the voxels in the group of voxels, described above, $\lambda_1$ is smaller than $K_{\lambda_1}$, wherein $K_{\lambda_1}$ equals about 0.0017 mm²/sec, the confidence of a diagnosis of cancer within the voxels is increased when, in addition, $\lambda_1$-$\lambda_3$ is smaller than $B_{\lambda_1-\lambda_3}$, wherein $B_{\lambda_1-\lambda_3}$ equals about 0.0006 mm²/sec, in at least some of the voxels in the group of voxels. According to some embodiments, diffusion ellipsoids having $\lambda_1$ values smaller than $K_{\lambda_1}$ and $\lambda_1$-$\lambda_3$ values smaller than $B_{\lambda_1-\lambda_3}$ are displayed differently to the other diffusion ellipsoids. According to some embodiments, wherein the target tissue is breast tissue, wherein $\lambda_1$ is smaller than about 0.0017 mm²/sec in a voxel, the confidence of a diagnosis of cancer within the voxel is increased when, in addition, $\lambda_1$-$\lambda_3$ is smaller than about 0.0006 mm²/sec in the voxel. Without being bound by any theory or mechanism, it is believed that the higher the cancer cellularity of a tumor, the lower the diffusion coefficients, and the more aggressive the tumor.

According to some embodiments, wherein the target tissue is breast tissue, a diffusion ellipsoid map of the target tissue is generated. In the map, diffusion ellipsoids with $\langle\lambda\rangle$ values lower than $K_{\langle\lambda\rangle}$, wherein $K_{\langle\lambda\rangle}$ equals about 0.0015 mm²/sec, are displayed differently to the other diffusion ellipsoids. In particular, diffusion ellipsoids, respectively associated with voxels in a group of voxels, such as the group described above, which includes adjacent voxels, are displayed differently to diffusion ellipsoids with $\langle\lambda\rangle$ values greater than $K_{\langle\lambda\rangle}$. The map thereby indicates a potential presence of cancer cells within the group of voxels. According to some embodiments, wherein the target tissue is breast tissue, a value of $\langle\lambda\rangle$ lower than about 0.0015 mm²/sec, in a voxel, indicates a presence of cancer cells within the voxel.

According to some embodiments, wherein the target tissue is breast tissue, a diffusion ellipsoid map of the target tissue is generated. In the map, diffusion ellipsoids with $\lambda_1$-$\lambda_3$ values lower than $B_{\lambda_1-\lambda_3}$, wherein $B_{\lambda_1-\lambda_3}$ equals about 0.0006 mm²/sec, are displayed differently to diffusion ellipsoids with $\lambda_1$-$\lambda_3$ values greater than $B_{\lambda_1-\lambda_3}$. In particular, diffusion ellipsoids, respectively associated with voxels in a group of voxels—which is similar to the group described above, which includes adjacent voxels, except that the voxels now are characterized by $\lambda_1$-$\lambda_3$ values lower than $B_{\lambda_1-\lambda_3}$ (rather than M values lower than K)—are displayed differently to diffusion ellipsoids with $\lambda_1$-$\lambda_3$ values greater than $B_{\lambda_1-80\ 3}$. The map thereby indicates a potential presence of cancer cells within the group of voxels. According to some embodiments, wherein the target tissue is breast tissue, a value of $\lambda_1$-$\lambda_3$ lower than about 0.0006 mm²/sec, in a voxel, indicates a presence of cancer cells within the voxel.

According to some embodiments, wherein the target tissue is breast tissue, a diffusion ellipsoid map of the target tissue is generated. In the map, diffusion ellipsoids with values of $\lambda_1$ lower than $K_{\lambda_1}$, wherein $K_{\lambda_1}$ equals about 0.0017 mm²/sec, and values of $\lambda_1$-$\lambda_3$ lower than $B_{\lambda_1-\lambda_3}$, wherein $B_{\lambda_1-\lambda_3}$ equals about 0.0006 mm²/sec, are displayed differently to the other diffusion ellipsoids. In particular, diffusion ellipsoids, respectively associated with voxels in a group of voxels—which is similar to the group described above (which includes adjacent voxels) except that the voxels now are further characterized by also having $\lambda_1$-$\lambda_3$ values lower than $B_{\lambda_1-\lambda_3}$—are displayed differently to the other diffusion ellipsoids. The map thereby indicates a potential presence of cancer cells within the group of voxels. According to some embodiments, wherein the target tissue is breast tissue, values of $\lambda_1$ and $\lambda_1$-$\lambda_3$ lower than about 0.0017 mm²/sec and about 0.0006 mm²/sec, respectively, in a voxel, indicate a presence of cancer cells within the voxel.

According to some embodiments, cancers characterized by values of M lower than K' are generally more aggressive than cancers characterized by values of M greater than (or equal to) K' and smaller than K. Thus, mapping tissues according to the methods disclosed herein may indicate the staging of the detected tumor.

According to some embodiments, the target tissue is prostate tissue. According to some such embodiments, wherein the target tissue is in the peripheral zone of the prostate, a diffusion ellipsoid map of the target tissue is generated. In the map, diffusion ellipsoids with $\lambda_1$ values lower than $K_{\lambda_1}$, wherein $K_{\lambda_1}$ equals about 0.0020 mm²/sec, are displayed differently to the other diffusion ellipsoids. In particular, diffusion ellipsoids, respectively associated with voxels in a group of voxels, such as the group described above, which includes adjacent voxels, are displayed differently to diffusion ellipsoids with $\lambda_1$ values greater than $K_{\lambda_1}$. The map thereby indicates a potential presence of cancer cells within the group of voxels. According to some embodiments, wherein the target tissue is in the peripheral zone of the prostate, a value of $\lambda_1$ lower than about 0.0020 mm$^2$/sec, in a voxel, indicates a presence of cancer cells within the voxel.

According to some embodiments, wherein the target tissue is in the peripheral zone of the prostate, M=$\lambda_1$, and I=1-FA, and wherein in each of the voxels in the group of voxels, described above, $\lambda_1$ is smaller than $K_{\lambda_1}$, wherein $K_{\lambda_1}$ equals about 0.0020 mm$^2$/sec, the confidence of a diagnosis of cancer within the voxels is increased when, in addition, 1-FA is smaller than $J_{1-FA}$, where $J_{1-FA}$ is set between about 0.7 to about 0.9, in at least some of the voxels in the group of voxels. According to some embodiments, diffusion ellipsoids having $\lambda_1$ values smaller than $K_{\lambda_1}$ and 1-FA values smaller than $J_{1-FA}$ are displayed differently to the other diffusion ellipsoids. According to some embodiments, wherein the target tissue is in the peripheral zone of the prostate, wherein $\lambda_1$ is smaller than about 0.0020 mm$^2$/sec in a voxel, the confidence of a diagnosis of cancer within the voxel is increased when, in addition, 1-FA is smaller than about 0.9, about 0.8, or about 0.7, in the voxel.

Without being bound by any theory or mechanism, it is believed that the higher the cancer cellularity of a tumor, the lower the diffusion coefficients, and the more aggressive the tumor.

According to some embodiments, wherein the target tissue is in the peripheral zone of the prostate, a diffusion ellipsoid map of the target tissue is generated. In the map, diffusion ellipsoids with $\langle\lambda\rangle$ values lower than $K\langle\lambda\rangle$, wherein $K\langle\lambda\rangle$ equals about 0.0016 mm$^2$/sec, are displayed differently to the other diffusion ellipsoids. In particular, diffusion ellipsoids, respectively associated with voxels in a group of voxels, such as the group described above, which includes adjacent voxels, are displayed differently to diffusion ellipsoids with $\langle\lambda\rangle$ values greater than $K\langle\lambda\rangle$. The map thereby indicates a potential presence of cancer cells within the group of voxels. According to some embodiments, wherein the target tissue is in the peripheral zone of the prostate, a value of $\langle\lambda\rangle$ lower than about 0.0016 mm$^2$/sec, in a voxel, indicates a presence of cancer cells within the voxel.

According to some embodiments, wherein the target tissue is in the peripheral zone of the prostate, a diffusion ellipsoid map of the target tissue is generated. In the map, diffusion ellipsoids with 1-FA values lower than $J_{1-FA}$, wherein $J_{1-FA}$ equals about 0.9, or about 0.8, or even about 0.7, are displayed differently to diffusion ellipsoids with 1-FA values greater than $J_{1-FA}$. In particular, diffusion ellipsoids, respectively associated with voxels in a group of voxels—which is similar to the group described above, which includes adjacent voxels, except that the voxels now are characterized by 1-FA values lower than $J_{1-FA}$ (rather than M values lower than K)—are displayed differently to diffusion ellipsoids with 1-FA values greater than $J_{1-FA}$. The map thereby indicates a potential presence of cancer cells within the group of voxels.

According to some embodiments, wherein the target tissue is in the peripheral zone of the prostate, a value of 1-FA lower than about 0.9, in a voxel, indicates a presence of cancer cells within the voxel. According to some embodiments, wherein the target tissue is in the peripheral zone of the prostate, a value of 1-FA lower than about 0.8, in a voxel, indicates a presence of cancer cells within the voxel. According to some embodiments, wherein the target tissue is in the peripheral zone of the prostate, a value of 1-FA lower than about 0.7, in a voxel, indicates a presence of cancer cells within the voxel.

According to some embodiments, wherein the target tissue is in the peripheral zone of the prostate, a diffusion ellipsoid map of the target tissue is generated. In the map, diffusion ellipsoids with values of $\lambda_1$ lower than $K_{\lambda_1}$, wherein $K_{\lambda_1}$ equals about 0.0020 mm$^2$/sec, and values of 1-FA lower than $J_{1-FA}$, wherein $J_{1-FA}$ is set between about 0.7 to about 0.9, are displayed differently to the other diffusion ellipsoids. In particular, diffusion ellipsoids, respectively associated with voxels in a group of voxels—which is similar to the group described above, which includes adjacent voxels, except that the voxels now are further characterized by also having 1-FA values lower than $J_{1-FA}$—are displayed differently to the other diffusion ellipsoids. The map thereby indicates a potential presence of cancer cells within the group of voxels. According to some embodiments, wherein the target tissue is in the peripheral zone of the prostate, values of $\lambda_1$ and 1-FA lower than about 0.0020 mm$^2$/sec and lower than a value within the range of about 0.7 to about 0.9, respectively, in a voxel, indicate a presence of cancer cells within the voxel.

Similarly, according to some embodiments, when the target tissue is in the central zone of the prostate, $K_{\lambda_1}$ equals about 0.0016 mm$^2$/sec, $K\langle\lambda\rangle$ equals about 0.0013 mm$^2$/sec, and $J_{1-FA}$ is set between about 0.6 to between about 0.8, as further elaborated on below in the description of FIGS. 14-19.

The skilled person will appreciate that diffusion ellipsoid maps of slabs obtained by a different partitioning of target tissue 100, e.g. a coronal partitioning, a sagittal partitioning, or an oblique partitioning, may also be provided, essentially as described above with respect to axial partitioning.

System

The present disclosure can be realized in hardware, software, or a combination of hardware and software. For example, the present disclosure can be realized as a computer system including customized components, such as one or more customized signal processors, configured to analyze DTI scan data, and one or more graphics processing units, configured to display and manipulate the diffusion ellipsoid maps disclosed herein (e.g. diffusion ellipsoid map 200). The one or more graphics processing units may be configured to enable a three-dimensional graphical representation of the diffusion ellipsoids in the diffusion ellipsoid maps, including light and shade effects. Manipulation of the diffusion ellipsoid maps may include, for example, tilting or rotating the map plane, or recoloring the diffusion ellipsoids as a user modifies/continuously modifies the value of the threshold K.

A system, according to the teachings herein, may be realized in a centralized fashion in one computer system or in a distributed fashion, where different elements are spread across several interconnected computer systems. Any kind of computer system—or other apparatus adapted for generating the diffusion ellipsoid maps described herein—is suited. A typical combination of hardware and software could be a general-purpose computer system with a computer program that, when loaded and executed, is configured to control the computer system such that it generates the diffusion ellipsoid maps described herein.

An embodiment of the present disclosure can also be embedded in a computer program product, which includes all the features enabling the generation of the diffusion ellipsoid maps described herein, and which—when loaded in a computer system—is able to generate these diffusion ellipsoid maps. The terms "computer program means" or "computer program" in the present context are interchangeable and refer to any expression, in any language, code or notation, of a set of instructions intended to cause a system having an information processing capability to perform a particular function either directly or after either or both of the following a) conversion to another language, code, or notation; and b) reproduction in a different material form.

A computer system may include, inter alia, one or more computers and at least a computer readable medium, allowing a computer system, to read data, instructions, messages or message packets, and other computer readable information from the computer readable medium. The computer readable medium may include non-volatile memory, such as ROM, Flash memory, Disk drive memory, CD-ROM, and other permanent storage. Additionally, a computer readable medium may include, for example, volatile storage such as RAM, buffers, cache memory, and network circuits. Further, the computer readable medium may include computer readable information in a transitory state medium such as a network link and/or a network interface, including a wired network or a wireless network that allows a computer system to read such computer readable information.

FIG. 3 schematically depicts a block-diagram of an example embodiment of a computer system 300, which may be used to generate a diffusion ellipsoid map, such as diffusion ellipsoid map 200. Computer system 300 includes a processor 302, a memory 304, a communication interface 306, and a linking interface 308.

Processor 302 may include one or more microprocessors, application-specific integrated circuits (ASICs), field-programmable gate arrays (FPGAs), firmware, and/or the like (all not shown). In particular, processor 302 may include one or more customized signal processors for analyzing DTI scan data, and optionally other types of scan data, such as $T_2$-weighted MRI scan data (and/or $T_1$-weighted MRI scan data), as well as other types of MRI scan data, such as dynamic contrast-enhanced (DCE) MRI data.

Memory 304 may include transitory memory components and/or non-transitory memory components (all not shown), which may be solid-state, magnetic, photonic, and/or the like. According to some embodiments, some or all of the memory components may be integrated together or distributed. According to some embodiments, some of the memory components may be external to computer system 300. According to some embodiments, memory 304 may be wholly or partially integrated with processor 302.

Communication interface 306 may be configured to send/receive information, e.g. to/from an external network or computer. In particular, communication interface 306 may be configured to functionally associate computer system 300 with an MRI scanner, thereby allowing to directly receive DTI scan data from the MRI scanner. Communication interface 306 may include wires, such as, Ethernet wires, and/or wireless technology, such as Wi-Fi, Bluetooth, and/or the like. According to some embodiments, communication interface 306 may be wholly or partially integrated with processor 302.

Linking interface 308 is configured to functionally associate processor 302, memory 304, and communication interface 306. According to some embodiments, linking interface 308 may be a system bus or a network.

Computer system 300 is functionally associated with a user interface 320. According to some embodiments, computer system 300 includes user interface 320. According to some embodiments, user interface 320 is not included in computer system 300 and the functional association there between is facilitated by communication interface 306, for example, via a network cable or via Wi-Fi. User interface 320 allows a user to control computer system 300, for example, to select which slice (of a DTI scanned target tissue) is presented (as a diffusion ellipsoid map) on a graphical display 322. Other control features of user interface 320 are detailed in the description of FIG. 5 below. According to some embodiments, user interface 320 includes graphical display 322. According to some embodiments, graphical display 322 is a touch screen.

According to some embodiments, computer system 300 is an image processing system, including customized components for image processing MRI scan data, such as customized signal processors and graphics processing units.

According to some embodiments, computer system 300 is integrated within an MRI scanner.

Method

FIG. 4 depicts a flowchart of a computer-implemented method 400 for mapping a target tissue, such as target tissue 100, of a subject, based on DTI scan data of the target tissue. Method 400 may be implemented in full, or in part, using a computer system, such as computer system 300. Method 400 includes:

A step 402, wherein the computer system receives DTI scan data of a plurality of voxels, such as voxels 140, in one or more slices, such as slice 130a or slices 130, of the target tissue.

A step 404, wherein for each voxel, the computer system determines a respective diffusion tensor (D), based on the DTI scan data.

A step 406, wherein the computer system determines for each voxel eigenvalues and eigenvectors of the respective diffusion tensor and a respective diffusion parameter (M), indicative of a magnitude of the diffusion in the voxel.

A step 408, wherein the computer system partitions the voxels into two groups, such that voxels, whose respective diffusion parameter is smaller than a threshold, are assigned to a first group of the two groups, and the other voxels are assigned to the second group.

A step 410, wherein the computer system produces a graphical representation of a diffusion ellipsoid map of one of the one or more slices, such as diffusion ellipsoid map 200. The diffusion ellipsoid map is characterized by (i) each diffusion ellipsoid therein being centered about respective map coordinates corresponding to a position in the slice of a respective voxel from the plurality; (ii) each diffusion ellipsoid therein having dimensions and an orientation determined by the eigenvalues and eigenvectors of the respective voxel; and (iii) diffusion ellipsoids therein, associated with voxels in the first group (e.g. diffusion ellipsoids enclosed within first closed curve 260 in FIG. 2a), being displayed differently to the other diffusion ellipsoids.

The term "displayed differently", as used herein with respect to the graphical representation of diffusion ellipsoids in a diffusion ellipsoid map (e.g. diffusion ellipsoid map 200), according to some embodiments, refers to a visual indication (e.g. marking, sign, feature), such as the coloring of a diffusion ellipsoid, which distinguishes ellipsoids in a first group of diffusion ellipsoids, for example, diffusion ellipsoids whose diffusion parameter is smaller than the threshold K (that is to say, diffusion ellipsoids corresponding to voxels in the first group of voxels), from diffusion ellipsoids in a second group (that is to say, diffusion ellipsoids corresponding to voxels in the second group of voxels). The visual indication is not topical, in the sense that the position of a diffusion ellipsoid does not signify whether the ellipsoid is, or is not, "displayed differently" to any other diffusion ellipsoid (that is to say, the position of a diffusion ellipsoid does not signify to which of the two groups the diffusion ellipsoid is assigned). In particular, a pair of diffusion ellipsoids may be "displayed identically" even though centered about different map coordinates, e.g. when both ellipsoids have diffusion parameters greater than the threshold, and consequently, according to some embodiments, colored in the same color, as depicted, for example, in FIG. 2a (see, for example, a second diffusion ellipsoid 210b and a third diffusion ellipsoid 210c in FIG. 2a).

According to some embodiments, diffusion ellipsoids, in a first group of diffusion ellipsoids can be said to be "displayed differently" from diffusion ellipsoids, in a second group of diffusion ellipsoids, even when the diffusion ellipsoids in the second group are not graphically represented, or colored in the same color as a background color of the diffusion ellipsoid map. For example, according to some embodiments, only diffusion ellipsoids with a diffusion parameter M (e.g. $\lambda_1$) smaller than the corresponding threshold K (e.g. $K_{\lambda_1}$) are displayed in the diffusion ellipsoid map.

According to some embodiments, as depicted in FIG. 4, step 404, step 406, and step 408, are performed in a loop: Following step 402, when step 404 is first performed, a first voxel from the plurality is selected, and the diffusion tensor thereof is determined. Steps 406 and 408 are then performed with respect to the first voxel. Next, step 404 is repeated with respect to a second voxel. That is to say, a second voxel (other from the first voxel) is selected, and the diffusion tensor thereof is determined. Steps 406 and 408 are then performed with respect to the second voxel, and so on until steps 404-408 are performed (once) with respect to each voxel in the plurality.

According to some embodiments, not depicted in FIG. 4, steps 404-408 are performed serially without repetition. That is to say, in step 404, the diffusion tensors of all the voxels in the plurality of voxels are determined, prior to proceeding to step 406. In step 406, the respective eigenvalues and eigenvectors of each of the diffusion tensors, and the associated diffusion parameters, are determined, prior to proceeding to step 408. In step 408, each of the voxels is assigned to either the first group or the second group, prior to proceeding to step 410.

According to some embodiments, in step 410, the graphical representation of the diffusion ellipsoid maps may be provided on a graphical display, such as, graphical display 322, or as computer readable information (e.g. encoded in a file on a computer readable medium). According to some embodiments, the graphical representation of the diffusion ellipsoid maps may be provided printed out on paper.

According to some embodiments, step 406, step 408, and step 410, are modified as follows: Step 406 further includes determining, for each voxel, a respective set of diffusion parameters.

The set of diffusion parameters includes the diffusion parameter M and additional diffusion parameters, which may be indicative of one or more additional characteristics of diffusion, such as an anisotropy of the diffusion. According to some embodiments, at least some of the additional diffusion parameters may also be indicative of the magnitude of the diffusion. For example, according to some embodiments, the diffusion parameter M may equal $\lambda_1$ while the additional diffusion parameter may equal $\langle\lambda\rangle$. Each of the additional diffusion parameters has a respective threshold associated therewith. In step 408, voxels, whose respective diffusion parameter is smaller than the threshold and whose respective additional diffusion parameters are each smaller than the respective threshold corresponding thereto, are assigned to the first group. In step 410, ellipsoids, whose respective voxels are assigned to the first group, are displayed differently to the other ellipsoids.

According to some embodiments, the additional diffusion parameters include, or consist of, an anisotropy parameter (A) indicative of an anisotropy of the diffusion. According to some embodiments, A may equal, or substantially equal, $\lambda_1$-$\lambda_3$—the absolute maximal anisotropy index. According to some embodiments, A may equal, or substantially equal, FA, RA, or 1-VR. According to some embodiments, the additional diffusion parameters include, or consist of, an isotropy parameter (I) indicative of an isotropy of the diffusion. According to some embodiments, I may equal, or substantially equal, 1-FA. According to some embodiments, I may equal, or substantially equal, (1-RA) or VR.

According to some embodiments, the diffusion parameter M, the anisotropy parameter A, and/or the isotropy parameter I, are computed using the eigenvalues of the obtained diffusion tensor D. According to some embodiments, M may be computed directly from D, rather than from the eigenvalues thereof. According to some embodiments A and/or I may be computed directly from D, rather than from the eigenvalues thereof. For example, according to some embodiments, M equals the largest component from among the three components along the diagonal of D, that is to say, $M=\max_i D_{ii}$. According to some embodiments, M is computed from a subset of the measurement data used to obtain D, for example, from the measurement data associated with three sets of measurements, each associated with the application of a magnetic field gradient in a different direction. According to some embodiments, M is computed prior to determining D, that is to say, independently of D. (Note that in such embodiments steps 404 and 406 are modified such that M is computed in step 404 instead of in step 406.)

The DTI scan data received in step 402 may be collected using DTI protocols (magnetic pulse sequences) known in the art, such as, or based on, the echo planar imaging (EPI) protocols reported in R. Turner et al., Radiology. 1990 November; 177(2):407-14, and R. Turner, et al., Magn Reson Med. 1991 June; 19(2):247-53, the twice-refocused spin echo EPI protocol reported in T. G. Reese et al., Magn. Reson. Med. 49:177-182 (2003), or the spatio-temporal encoding protocol reported in E. Solomon et al., Magn. Reson. Med. 2015 June; 73(6):2163-73; the contents of (all four of) which are incorporated herein by reference.

According to some embodiments, the DTI scan data received in step 402 is collected using the readout-segmented EPI protocol reported in S. J. Holdsworth et al., Eur J Radiol. 2008; 65(1):36-46; the contents of which are incorporated herein by reference.

The DTI scan data may include data collected from multiple DTI scans (e.g. at b=700 sec/mm², where b is the so called b value or diffusion weighting, which is proportional to the magnitude of the gradient pulse); each DTI scan involving the application of a magnetic field gradient (diffusion gradient) in one out of a set of spatial directions (e.g. 32 directions or 64 directions). The skilled person will appreciate that the number of directions may be changed, such as to obtain a desired trade-off between the spatial resolution and the scan time, since increasing the number of directions, increases the spatial resolution, but at the expense of the scan time. For example, using current state-of-the-art technology (e.g. the Siemens Trio 3 Tesla whole body MRI scanner and transmitting and receiving coils, as detailed below in the description of FIGS. 5a-13) a diffusion ellipsoid map of the breast having a spatial resolution of about 2 mm×2 mm×2 mm (e.g. $a_1$, $a_2$, $a_3$=2 mm) can be obtained when employing about 32 directions in an overall scan time of about 6 minutes.

Typically, additional scan data beyond the DTI scan data are received by the computer system, in particular, $T_2$-weighted scan data (collected at b=0 sec/mm²). As known in the art, $T_2$-weighted scan data corresponding to voxels located outside the body of the subject (e.g. outside of breast 120) may be used to determine the maximum noise level, as well as to provide the anatomical outline and the main anatomical features of the scanned tissue/organ. Typically, voxels for which the obtained DTI scan signal intensities are not above the maximum noise level are not subjected to any further processing (i.e. the respective diffusion tensors are not determined and no ellipsoid will be displayed on the respective map coordinates in the diffusion ellipsoid map provided in step 410). Further, in step 404, the $T_2$-weighted scan data may be used to normalize the DTI scan. The normalized data is used to determine the diffusion tensors corresponding to the voxels, e.g. according to the Stejeskal-Tanner equation (E. O. Stejskal and J. E. Tanner, J. Chem. Phys. 42: 288-292, 1965), by applying a non-linear best-fit regression algorithm (as detailed, for example, in N. Nissan et al., J. Vis. Exp. (94), e52048, 2014).

According to some embodiments, DCE data may additionally be received.

According to some embodiments, the DTI scan further includes fat suppression, as known in the art.

According to some embodiments, the DTI scan data may be received directly from the MRI scanner, which effected the DTI scan, e.g. by communicatively associating the computer system with the MRI scanner, for example, via an Ethernet cable or wirelessly via Wi-Fi.

According to some embodiments, the DTI scan data may be received from another computer system, e.g. via Wi-Fi. According to some embodiments, the DTI scan data may be received from a non-transient computer readable medium, such as a hard-disk, a CD-ROM, a USB drive, and/or the like.

The determination of each of the diffusion tensors in step 404 may in principal be performed using brain DTI software generally provided with commercial MRI scanners, after appropriate modifications for imaging the target tissue (when the target tissue is not the brain). The determination of the diffusion tensor may also be performed using customized software, such as, the C++ homebuilt software package for imaging the breast, e.g. as described in N. Nissan et al., J. Vis. Exp. (94), e52048, doi:10.3791/52048 (2014). The C++ homebuilt software package was used for producing the maps described below in the description of FIGS. 5a-13.

The determination of the respective eigenvalues and eigenvectors of each of the diffusion tensors in step 406 may be carried out by applying principal component analysis (PCA), or any other diagonalizing program, as known in the art.

According to some embodiments, in step 410, the diffusion ellipsoid map of a slice may be superimposed on a $T_2$-weighted image of same to facilitate identifying the position of each ellipsoid relative to the target tissue, as elaborated on below, e.g. in the description of FIGS. 6a-6b when the target tissue is breast tissue.

According to some embodiments, graphical representations of other types of diffusion ellipsoid maps may additionally be provided, such as diffusion ellipsoid maps wherein the color of each ellipsoid is based on the orientation of the respective $v_1$. According to some embodiments, vector maps of e.g. $v_1$ may additionally be provided. According to some embodiments, graphical representations of other types of DTI maps of the target tissue may also be provided, such as parametric maps of, for example, $\lambda_1$, $<\lambda>$, $\lambda_1$-$\lambda_3$, normalized anisotropy indices (e.g. the relative anisotropy (RA) or the fractional anisotropy (FA)), or isotropy indices (e.g. 1-FA), wherein each voxel is in a slice is colored according to the respective value thereof.

According to some embodiments, a number of diffusion ellipsoid maps, corresponding to different slices of the target tissue, for example, adjacent slices, may simultaneously be graphically represented, for example, side-by-side on graphical display 322. According to some embodiments, non-parallel slices, for example, perpendicular slices, may be simultaneously graphically represented. The user may select how to slice the target tissue, e.g. into slices 130 or into sagittal slices, and which slices are to be graphically represented. For example, slice 130a may be displayed next to one or more slices oriented at respective angles relative thereto.

According to some embodiments, the diffusion tensor D is a symmetric $4^{th}$-order tensor in accordance with the $4^{th}$-order DTI model described in Teruel et al., ibid, and in references therein. In such embodiments, the diffusion parameter M may be taken as, for example, the largest of the eigenvalues of D or the apparent diffusion coefficient associated with D (see Teruel et al., ibid., and references therein, for the definitions of these quantities).

Clinical Data

FIGS. 5a-13 present diffusion ellipsoid maps of respective slabs of breast tissue, generated according to some of the embodiments disclosed herein. The diffusion ellipsoid maps were generated from axial DTI scan data of 60 slices with fat suppression and acceleration factor 2, of spin-echo twice-refocused EPI sequences (echo planar imaging) with four gradients to compensate for eddy currents, and with b=0 sec/mm² and b=700 sec/mm² (see Degani, ibid.). Scan parameters included a repetition time (TR) of 10,400 msec, and a resolution of 1.9 mm×1.9 mm×1.9-2.5 mm. In FIGS. 5a-7, diffusion gradients were applied in 30 or 64 directions (corresponding to acquisition times of approximately 6 minutes and 12 minutes, respectively) with an echo time (TE) of 120 msec leading to a diffusion time of 44 msec. (It is noted that unlike in standard (i.e. non-twice refocused) EPI sequences, in twice-refocused EPI sequences the diffusion time generally does not equal half the echo time.) In FIGS. 8a-13, diffusion gradients were applied in 20 directions (corresponding to an acquisition time of approximately 4 minutes), with TE=120 msec.

It is noted that diffusion ellipsoid maps of breast tissue of similar quality as those depicted in FIGS. 5a-13 may be obtained using b values as low as 600 sec/mm² or as high as 800 sec/mm², and echo times as low as 110 msec or as high as 130 msec, leading to diffusion times as low as approximately 40 msec and as high as approximately 50 msec, respectively.

According to some embodiments, standard EPI protocols may be employed, with echo times which may be as low as 80-100 msec, and b-values ranging from 400 sec/mm² to 1000 sec/mm².

The DTI scan data were collected on a Siemens Trio 3 Tesla whole body scanner, using a transmitting body coil and a receiving four-channel breast array-coil (Siemens) for small to medium sized breasts and a seven-channel breast array coil (In-vivo, Orlando, Fla.) for large sized breasts.

As mentioned above, low $\lambda_1$ or $\langle\lambda\rangle$ values are indicative of cancer. Alternatively or additionally, low $\lambda_1-\lambda_3$ may also be indicative of cancer. In particular, values of $\lambda_1$ smaller than a threshold value of about 0.0017 mm$^2$/sec are indicative of malignant breast tumors, while benign breast tumors and healthy breast tissue are characterized by values of $\lambda_1$ of about 0.0018-0.0019 mm$^2$/sec and about 0.0024-0.0025 mm$^2$/sec, respectively. Values of $\langle\lambda\rangle$, smaller than about 0.0015 mm$^2$/sec, are also indicative of malignant breast tumors. Values of $\lambda_1-\lambda_3$, smaller than about 0.0006 mm$^2$/sec, may also be indicative of malignant breast tumors. These thresholds were obtained from clinical statistics collected over the last few years by the Applicant and colleagues, as elaborated on in scientific publications of the Applicant, such as Eyal et al., ibid.

According to some embodiments, the thresholds are based on receiver operating characteristic (ROC) curve analysis that determines the sensitivity and specificity. The threshold that yields the best sensitivity and specificity, for differentiating malignant tumors from benign tumors and health tissue, is selected. ROC curve analysis is detailed, for example, in C. E. Metz et al., Statist. Med. 17, 1033-1053 (1998).

In FIGS. 5a-13 the diffusion ellipsoids are colored in an RGB color scale between red and purple (with the bottom end of the scale colored in red and the top end of the scale colored in purple). Some of the Figures vary in the choice of the diffusion rate parameter and the values corresponding to the bottom end and top end of the scale, respectively.

FIGS. 5a-5c present diffusion ellipsoid maps of a slab in a breast of a 41 year old female subject with a malignant tumor, wherein the diffusion ellipsoids are colored according to the value of $\lambda_1$. More specifically, the diffusion parameter M was taken as $\lambda_1$.

In FIG. 5a the diffusion ellipsoid map was generated such that the upper end of the color scale, indicating the value of $\lambda_1$, corresponds to the threshold $K_{\lambda_1}=0.0017$ mm$^2$/sec, and the lower end of the color scale corresponds to the lower threshold $K_{\lambda_1}'=0.0008$ mm$^2$/sec. Accordingly, diffusion ellipsoids with $\lambda_1<K_{\lambda_1}'$ are colored in the same color (i.e. the darkest shade of red in the color scale), indicating a presence of cancer cells in the respective voxels. Diffusion ellipsoids with $K_{\lambda_1}>\lambda_1\geq K_{\lambda_1}'$ are colored according to the value of $\lambda_1$, indicating a potential presence of cancer cells in the respective voxels.

Diffusion ellipsoids with $\lambda_1\geq K_{\lambda_1}$ are colored in the same color (i.e. the darkest shade of purple in the color scale), indicating healthy tissue in the respective voxels. As used herein, "healthy tissue" is a relative terminology, generally referring to tumor-free tissue at the level of the statistical evaluation, and according to some embodiments, may refer to cancer-free tissue, or breast cancer free tissue. According to some embodiments, "healthy breast tissue" refers to cancer-free tissue at the level of the statistical evaluation.

FIG. 5b differs from FIG. 5a in that the lower end of the color scale does not correspond to $K_{\lambda_1}'$, corresponding instead to 0 mm$^2$/sec. Even though diffusion ellipsoids with $\lambda_1<K_{\lambda_1}'$ and diffusion ellipsoids with $K_{\lambda_1}>\lambda_1\geq K_{\lambda_1}'$ are still colored distinctly, as compared to FIG. 5a, the distinction is potentially harder to spot with the naked eye.

FIG. 5c differs from FIG. 5a in that the upper end of the color scale does not correspond to $K_{\lambda_1}$, extending beyond $K_{\lambda_1}$ until 0.0030 mm$^2$/sec. Even though diffusion ellipsoids with $\lambda_1\geq K_{\lambda_1}$ and diffusion ellipsoids with $\lambda_1<K_{\lambda_1}$ are still colored distinctly, as compared to FIG. 5a, the distinction may be harder to spot with the naked eye, thereby potentially, in some cases, complicating the detection of cancer.

In FIGS. 6a-6b, the diffusion ellipsoid maps of FIGS. 5a-5b, respectively, are shown superimposed on a $T_2$-weighted image of the breast of the subject, thereby indicating the respective locations of the diffusion ellipsoids relative to the breast.

FIGS. 7a-7c differ from FIGS. 5a-5c in that the diffusion ellipsoids therein are colored according to the value of $\langle\lambda\rangle$. More specifically, in FIGS. 7a-7c the diffusion parameter M was taken as $\langle\lambda\rangle$. In FIG. 7a, the upper end of the color scale corresponds to the threshold $K_{\langle\lambda\rangle}=0.0015$ mm$^2$/sec, and the lower end of the color scale corresponds to the lower threshold $K_{\langle\lambda\rangle}'=0.0008$ mm$^2$/sec. In FIG. 7b, the lower end of the color scale corresponds to $\langle\lambda\rangle=0$ mm$^2$/sec. In FIG. 7c, the upper end of the color scale corresponds to $\langle\lambda\rangle=0.0030$ mm$^2$/sec. Similarly to FIG. 5a-5c, the distinction between potentially cancerous tissue and healthy tissue may be easiest to spot in FIG. 7a and hardest to spot in FIG. 7c.

FIG. 8 presents a diffusion ellipsoid map of a slab of a breast of a 39 year old female subject with a benign tumor (fibroadenoma), with a coloring scheme identical to that of FIG. 5a. As the scale color ranges between 0.0008-0.0017 mm$^2$/sec, and as benign breast tumors are generally characterized by $\lambda_1$ values of about 0.0018-0.0019 mm$^2$/sec, the benign tumor is not readily apparent in FIG. 8, thereby demonstrating the capacity of the method disclosed herein to distinguish between malignant and benign breast tumors, based on the generated diffusion ellipsoid maps.

FIG. 9 presents the diffusion ellipsoid map of FIG. 8 superimposed on a $T_2$-weighted image of the breast of the subject, thereby indicating the respective locations of the diffusion ellipsoids relative to the breast.

FIG. 10 presents a diffusion ellipsoid map of the slab imaged in FIG. 8, with a coloring scheme identical to that of FIG. 7a. Similarly to FIG. 8, the benign tumor is not readily apparent in FIG. 10, thereby demonstrating the capacity of the method disclosed herein to distinguish between malignant and benign breast tumors, based on the generated diffusion ellipsoid maps.

FIG. 11 presents a diffusion ellipsoid map of a slab of healthy breast tissue of a 65 year old female subject, with a coloring scheme identical to that of FIG. 5a. As the color scale ranges between 0.0008-0.0017 mm$^2$/sec, and as healthy breast tissue in pre- and post-menopausal women, or in lactating women, is generally characterized by $\lambda_1$ values of about 0.0021-0.0025 mm$^2$/sec, the coloring is generally uniform. (See N. Nissan et al., Radiology: Volume 271: Number 3—June 2014, the contents of which are incorporated herein by reference).

FIG. 12 presents the diffusion ellipsoid map of FIG. 11 superimposed on a $T_2$-weighted image of the breast of the subject, thereby indicating the respective locations of the diffusion ellipsoids relative to the breast.

FIG. 13 presents a diffusion ellipsoid map of the slab imaged in FIG. 11, with a coloring scheme identical to that of FIG. 7a. As the color scale ranges between 0.0008-0.0015 mm$^2$/sec, and as healthy breast tissue in pre- and post-menopausal women, or in lactating women, is generally characterized by $\langle\lambda\rangle$ values (sometime termed ADC) of about 0.0016-0.0022 mm$^2$/sec, the coloring is, for the most part, uniform. (See Nissan et al., Radiology, 271(3), 2014).

FIGS. 14-19 present diffusion ellipsoid maps of respective slabs of prostate tissues of 40 to 75 year old human males, generated according to some of the embodiments disclosed herein. The diffusion ellipsoid maps were generated from axial DTI scan data of 26 slices with fat suppression and acceleration factor 2, of spin-echo EPI sequences (echo planar imaging) with b=0 sec/mm$^2$ and b=600 sec/mm$^2$. Scan parameters included a repetition time (TR) of 4,160 msec, and a resolution of 1.4 mm×1.4 mm×3 mm. In FIGS. 14-19, diffusion gradients were applied in 32 directions (corresponding to acquisition times of approximately 5 minutes) with an echo time (TE) of 70 msec leading to a diffusion time of approximately 30 msec.

It is noted that diffusion ellipsoid maps of prostate tissue of similar quality as those depicted in the FIGS. 14-19 may be obtained using b values as low as 500 sec/mm$^2$ or as a high as 700 sec/mm$^2$, and echo times as low as 60 msec or as high as 85 msec, leading to diffusion times as low as approximately 25 msec and as high as approximately 40 msec, respectively.

According to some embodiments, standard EPI protocols may be employed, with echo times which may be as low as 60-85 msec, and b-values ranging from 400 sec/mm$^2$ to 1000 sec/mm$^2$.

The DTI scan data were collected on an Ingenia, Philips Medical Systems, 3 Tesla whole body scanner, using a 32 channel torso coil.

As mentioned above, low $\lambda_1$ or $\langle\lambda\rangle$ values are indicative of cancer. Alternatively or additionally, 1-FA values below threshold may also be indicative of cancer. In particular, values of $\lambda_1$ smaller than a threshold value of about 0.0020 mm$^2$/sec, in the peripheral zone of the prostate, are indicative of malignant prostate tumors therein (i.e. in the peripheral zone), while healthy prostate tissue in the peripheral zone is characterized by values of $\lambda_1$ of about 0.0021-0.0026 mm$^2$/sec. Values of $\lambda_1$ smaller than a threshold value of about 0.0016 mm$^2$/sec, in the central zone of the prostate, are indicative of malignant prostate tumors therein (i.e. in the central zone), while healthy prostate tissue in the central zone is characterized by values of $\lambda_1$ of about 0.0019-0.0023 mm$^2$/sec. Values of $\langle\lambda\rangle$ smaller than about 0.0016 mm$^2$/sec, in the peripheral zone of the prostate, are also indicative of malignant prostate tumors therein. Values of $\langle\lambda\rangle$ smaller than about 0.0013 mm$^2$/sec, in the central zone of the prostate, are also indicative of malignant prostate tumors therein. Values of 1-FA lower than about 0.9, about 0.8, or even about 0.7, may also be indicative of malignant prostate tumors in the peripheral zone. Values of 1-FA lower than about 0.8, about 0.7, or even about 0.6, may also be indicative of malignant prostate tumors in the central zone. These thresholds were obtained from clinical statistics.

FIG. 14 presents a diffusion ellipsoid map of a slab in a prostate of a male subject with a malignant tumor, wherein the diffusion ellipsoids are colored according to the value of $\lambda_1$. More specifically, the diffusion parameter M was taken as $\lambda_1$.

The diffusion ellipsoid map was generated such that the upper end of the color scale, indicating the value of $\lambda_1$, corresponds to the threshold $K_{\lambda_1}$=0.0020 mm$^2$/sec, and the lower end of the color scale corresponds to the lower threshold $K_{\lambda_1}'$=0.0006 mm$^2$/sec. Accordingly, diffusion ellipsoids with $\lambda_1 < K_{\lambda_1}'$ are colored in the same color (i.e. the darkest shade of red in the color scale), indicating a presence of cancer cells in the respective voxels. Diffusion ellipsoids with $K_{\lambda_1} \geq \lambda_1 \geq K_{\lambda_1}'$ are colored according to the value of $\lambda_1$, indicating a potential presence of cancer cells in the respective voxels.

Diffusion ellipsoids with $\lambda_1 \geq K_{\lambda_1}$ are colored in the same color (i.e. the darkest shade of purple in the color scale), indicating healthy tissue in the respective voxels. According to some embodiments, "healthy prostate tissue" refers to cancer-free tissue at the level of the statistical evaluation.

FIG. 15 differ from FIG. 14 in that the diffusion ellipsoids therein are colored according to the value of $\langle\lambda\rangle$. More specifically, in FIG. 15 the diffusion parameter M was taken as $\langle\lambda\rangle$. The upper end of the color scale corresponds to the threshold $K_{\langle\lambda\rangle}$=0.0016 mm$^2$/sec, and the lower end of the color scale corresponds to the lower threshold $K_{\langle\lambda\rangle}'$=0.0006 mm$^2$/sec.

As seen in FIGS. 14-15, potentially cancerous tissue is present both in the central zone and peripheral zones of the prostate.

FIG. 16 differs from FIG. 14 in that the upper end of the color scale corresponds to the threshold $K_{\lambda_1}$=0.0016 mm$^2$/sec (instead of 0.0020 mm$^2$/sec), which is the $\lambda_1$ threshold for cancer detection in the central zone of the prostate.

FIG. 17 differs from FIG. 15 in that the upper end of the color scale corresponds to the threshold $K_{\langle\lambda\rangle}$=0.0013 mm$^2$/sec (instead of 0.0016 mm$^2$/sec), which is the $\langle\lambda\rangle$ threshold for cancer detection in the central zone of the prostate.

The choice of $K_{\lambda_1}$ and $K_{\langle\lambda\rangle}$ in FIG. 16 and FIG. 17, respectively, visually facilitates the distinction between healthy tissue and potentially cancerous tissue in the central zone of the prostate.

In FIGS. 14-15, cancerous tissue is present both in central zones and peripheral zones of the prostate.

FIG. 18 presents a diffusion ellipsoid map of a slab of a prostate of a male subject with a malignant tumor, with a coloring scheme identical to that of FIG. 14.

FIG. 19 presents a diffusion ellipsoid map of the slab imaged in FIG. 18, with a coloring scheme identical to that of FIG. 15.

In FIGS. 18-19, potentially cancerous tissue is seen to be present in a peripheral zone of the prostate.

The skilled person will appreciate that diffusion ellipsoid maps of other internal bodily organs beyond the breast and the prostate gland may be generated using the systems and methods disclosed herein. Further, the diffusion ellipsoid maps disclosed herein may potentially be of utility for cancer detection in other internal bodily organs beyond the breast and the prostate.

As used herein, the terms "prostate" and "prostate gland" are interchangeable.

The skilled person will appreciate that the isotropy indices used herein in the description of prostate cancer, are used to simplify and uniformize the presentation of both the text and the Figures, and that corresponding anisotropy indices could have been used instead (e.g. FA instead of 1-FA). In fact, an anisotropy index may always be converted into an isotropy index by simply putting a minus sign in front of the anisotropy index and vice-versa.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A computer-implemented method of mapping a target tissue of a subject, the method comprising:
    providing diffusion tensor imaging (DTI) scan data of a plurality of voxels in one or more slabs of a target tissue of a subject;
    calculating a respective diffusion tensor for each voxel in the plurality of voxels in the target tissue;
    determining, for each voxel, eigenvalues and eigenvectors of the respective diffusion tensor and a respective set of diffusion parameters, wherein the respective set of diffusion parameters associated with each voxel is indicative of a magnitude and/or isotropy of the diffusion in the voxel;
    partitioning the voxels into two groups, a first group and a second group, wherein the voxels, whose respective set of diffusion parameters is such that each diffusion parameter is less than a corresponding element in a set of thresholds, are substantially all in the first group; and
    generating a graphical representation of a diffusion ellipsoid map made from diffusion ellipsoids associated with the first group and the second group of voxels of at least one of the one or more slabs of the target tissue,
    wherein the respective set of diffusion parameters, associated with each voxel, includes a diffusion rate parameter substantially equal to a convex combination of the eigenvalues of the voxel or to an apparent diffusion coefficient of the voxel,
    wherein the diffusion ellipsoids associated with voxels in the first group are colored differently to the diffusion ellipsoids associated with the second group,
    wherein each diffusion ellipsoid corresponding to the first group is displayed in a color scale, corresponding to a magnitude of the diffusion rate parameter,
    wherein each diffusion ellipsoid corresponding to the second group is displayed in a color from a group consisting of a color not in the color scale and a color at an upper end of the color scale, and
    wherein the target tissue is a prostate or a portion thereof.

2. The method of claim 1, wherein the voxels, whose respective set of diffusion parameters is such that at least one of the diffusion parameters is greater than, or equal to, a corresponding element in the set of thresholds are substantially all in the second group.

3. The method of claim 2, wherein the second group of voxels is partitioned into at least two subgroups, according to respective values of the set of diffusion parameters of the voxels in the second group.

4. The method of claim 3, wherein the second group is partitioned into two subgroups, a first subgroup and a second subgroup, and wherein voxels, whose diffusion rate parameter is smaller than the respective corresponding element in the set of thresholds, are substantially all in the first subgroup, and wherein voxels, whose diffusion rate parameter is greater than the respective corresponding element in the set of thresholds, are substantially all in the second subgroup,
    wherein the diffusion parameters consist of a diffusion rate parameter and an isotropy parameter.

5. The method of claim 1, wherein diffusion ellipsoids corresponding to the first group, whose respective diffusion parameter is smaller than a lower threshold, are displayed in a color at a bottom end of the color scale; the color scale being scaled such that the bottom end thereof corresponds to the lower threshold, and the top end thereof corresponds to the element in the set of thresholds associated with the diffusion rate parameter.

6. The method of claim 1, wherein the diffusion rate parameter is selected from the group consisting of substantially $\lambda_1$ and substantially $\langle \lambda \rangle$.

7. The method of claim 1, wherein the diffusion ellipsoid map including adjacent diffusion ellipsoids belonging to the first group, are indicative of cancer in the target tissue.

8. The method of claim 7, wherein the diffusion ellipsoid map including adjacent ellipsoids, which are displayed in a color corresponding to the bottom end of the color scale, are indicative of a more aggressive cancer in the target tissue, as compared to the diffusion ellipsoid maps including adjacent ellipsoids belonging to the first group, but which do not include adjacent ellipsoids displayed in the color corresponding to the bottom end of the color scale.

9. The method of claim 1, wherein the set of diffusion parameters includes an isotropy parameter indicative of an isotropy of the diffusion within a voxel.

10. The method of claim 9, wherein the isotropy parameter is substantially 1-FA, substantially 1-RA, or substantially VR.

11. The method of claim 1, wherein the diffusion tensor is a $4^{th}$-order tensor according to a $4^{th}$-order DTI model.

12. The method of claim 1, wherein substantially only voxels, associated with DTI scan data above a maximum noise level, are included in the plurality of voxels.

13. The method of claim 1, further comprising superimposing the diffusion ellipsoids on at least one MRI image of the target tissue.

14. A non-transitory computer readable medium having stored therein instructions executable by a computer system configured to implement the method of claim 1.

15. An image processing system for mapping a target tissue of a subject, the system comprising:
    a memory comprising computer executable instructions and data; and
    a processor functionally coupled to the memory and configured by the computer executable instructions, the processor being able to:
        receive DTI scan data of a plurality of voxels in one or more slabs of a target tissue of a subject;
        calculate, from the DTI scan data, a respective diffusion tensor for each voxel in the plurality of voxels in one or more slabs of the target tissue;

determine, for each voxel, eigenvalues and eigenvectors of the respective diffusion tensor and a respective set of diffusion parameters, wherein the respective set of diffusion parameters associated with each voxel is indicative of a magnitude and/or isotropy of the diffusion in the voxel;

partition the voxels into two groups, a first group and a second group, wherein the voxels, whose respective set of diffusion parameters is such that each diffusion parameter is less than a corresponding element in a set of thresholds, are substantially all in the first group; and generate a graphical representation of a diffusion ellipsoid map of at least one of the one or more slabs made from diffusion ellipsoids associated with the first group and the second group of voxels, wherein the respective set of diffusion parameters, associated with each voxel, includes a diffusion rate parameter substantially equal to a convex combination of the eigenvalues of the voxel or to an apparent diffusion coefficient of the voxel, wherein the diffusion ellipsoids associated with voxels in the first group, are colored differently to the diffusion ellipsoids associated with voxels in the second group, wherein each diffusion ellipsoid corresponding to the first group is displayed in a color scale, corresponding to a magnitude of the diffusion rate parameter, wherein each diffusion ellipsoid corresponding to the second group is displayed in a color from a group consisting of a color not in the color scale and a color at an upper end of the color scale, and wherein the target tissue is a prostate or a portion thereof.

* * * * *